US006969861B2

(12) United States Patent
Shoji et al.

(10) Patent No.: US 6,969,861 B2
(45) Date of Patent: Nov. 29, 2005

(54) CASSETTE FOR RADIOGRAPHIC IMAGING, RADIOGRAPHIC IMAGE READING APPARATUS AND RADIOGRAPHIC IMAGE READING METHOD

(75) Inventors: Takehiko Shoji, Hino (JP); Haruhiko Masutomi, Hino (JP); Tomoko Saito, Hino (JP); Masafumi Saito, Hino (JP); Kouji Amitani, Hachioji (JP); Masayuki Nakazawa, Hachioji (JP); Yoshiyuki Ishimitsu, Sayama (JP)

(73) Assignee: Konica Corporation, Tokyo (JP)

( * ) Notice: Subject to any disclaimer, the term of this patent is extended or adjusted under 35 U.S.C. 154(b) by 355 days.

(21) Appl. No.: 10/259,124

(22) Filed: Sep. 27, 2002

(65) Prior Publication Data

US 2003/0063708 A1 Apr. 3, 2003

(30) Foreign Application Priority Data

| Oct. 2, 2001 | (JP) | ............................. 2001-306592 |
| Dec. 14, 2001 | (JP) | ............................. 2001-381927 |
| Dec. 25, 2001 | (JP) | ............................. 2001-392030 |

(51) Int. Cl.$^7$ .......................... G03B 42/04; G01T 1/24; G21K 1/00
(52) U.S. Cl. .............................. 250/484.4; 250/363.1; 250/370.09; 250/370.11; 378/154
(58) Field of Search ...................... 250/370.09, 370.08, 250/370.01, 370.11, 580, 581, 582, 584, 585, 250/586, 589; 378/154, 155, 156

(56) References Cited

U.S. PATENT DOCUMENTS

| 5,259,016 A | * | 11/1993 | Dickerson et al. ........... 378/186 |
| 5,475,230 A | * | 12/1995 | Stumpf et al. ............ 250/484.4 |
| 5,581,592 A | * | 12/1996 | Zarnoch et al. .............. 378/154 |
| 5,661,309 A | * | 8/1997 | Jeromin et al. .............. 250/580 |
| 5,747,812 A | * | 5/1998 | DiFilippo ................. 250/363.1 |
| 5,818,065 A | * | 10/1998 | Exelmans .................... 250/588 |
| 6,191,426 B1 | * | 2/2001 | Hayakawa et al. ....... 250/484.4 |
| 6,252,938 B1 | * | 6/2001 | Tang ........................... 378/154 |
| 6,429,448 B1 | * | 8/2002 | Moore et al. ................. 250/585 |
| 6,501,829 B2 | * | 12/2002 | Matsumoto et al. ......... 378/154 |
| 2002/0003863 A1 | * | 1/2002 | Ohkoda ....................... 378/154 |

* cited by examiner

*Primary Examiner*—Albert Gagliardi
(74) *Attorney, Agent, or Firm*—Lucas & Mercanti LLP

(57) ABSTRACT

A housing for accommodating a radiation detecting member, has a first plate member to which radiation is incident from an outside of the housing; a second plate member arranged opposite to the first plate member; a radiation detecting member provided between the first plate member and the second plate member and having a radiation receiving surface to detect the radiation having passed through the first plate member; and a scattering radiation shielding member arranged at a radiation receiving surface side of the radiation detecting member and to eliminate scattering radiation from the radiation before the radiation is detected by the radiation receiving surface.

22 Claims, 30 Drawing Sheets

X-RAY

CASSETTE FOR RADIOGRAPHIC IMAGING, RADIOGRAPHIC IMAGE READING APPARATUS AND RADIOGRAPHIC IMAGE READING METHOD

BACKGROUND OF THE INVENTION

The present invention relates to a radiation image reading apparatus, and particularly to a radiation image reading apparatus which is used in a radiation image information recording and reproducing system using a radiation detector.

From the past, a radiation image represented by an X-ray image is widely used for the disease diagnosis. As a method to obtain the radiation image, so-called radiography system by which the radiation which passes through the subject is irradiated onto a fluorescent substance layer which is called an intensifying screen of the radiation detector, and a visible ray emitted from this fluorescent substance layer is irradiated onto the a silver halide photosensitive material (hereinafter, called "photosensitive material"), and a developing processing is conducted on this photosensitive material and a visible image is obtained, is proposed and put into practical use.

In recent years, instead of the radiography system, a radiation image recording and reproducing system in which the irradiated radiation energy is accumulated and recorded, and the radiation detector having a "stimulable phosphor" which stimulably emits corresponding to the accumulated and recorded radiation energy, when exciting light is irradiated, is used, is proposed. This system is structured in such a manner that, when the radiation transmitted the subject, is irradiated onto the sheet-like stimulable phosphor, after the radiation energy (hereinafter, called "image information") corresponding to the radiation transmittance density of each portion of the subject, is accumulated and recorded into the stimulable phosphor, the image information accumulated and recorded in the stimulable phosphor is emitted by the exciting light as the stimulable emission light, and the intensity of this stimulable emission light is converted into an electric signal, and through the image recording material such as the photosensitive material or an image display apparatus such as a CRT, it is reproduced as a visible image.

Sheet-like stimulable phosphor (hereinafter, called "stimulable phosphor sheet") 500 is, as shown in FIG. 37, in many cases, arranged in a housing 520 in the condition that it is fixed on a predetermined supporting plate 510, and used for the radiation image radiographing, and after the radiation image radiographing is completed, the image information accumulated in the stimulable phosphor is read out by a radiation image reading means (hereinafter, called "reading means") 530 provided in the housing 520. The radiation image radiographing apparatus provided with such a reading means 530 is called the "radiation image reading apparatus".

As the reading means 530, as shown in FIG. 37, a means arranged on the rear surface side (opposite side to the radiation source) of the stimulable phosphor sheet 500 is proposed, and put in practical use. This reading means is provided with an exciting light source 531, light guiding means 532, and photoelectric conversion means 533, and the image information accumulated on the stimulable phosphor sheet 500 is emitted as the stimulable emission light from the rear surface side by the exciting light irradiated from the exciting light source 531, and the stimulable emission light is guided to the photoelectric conversion means 533 through the light guiding means 532 and converted into an electric signal. This electric signal is transferred to an image processing means, not shown, and the image processing is conducted, and visualized.

When the radiation image reading apparatus provided with the reading means 530 which reads out the stimulable emission light emitted from the rear surface side (opposite side to the radiation source) of such the stimulable phosphor sheet 500, is used, there is a following problem.

That is, on the radiation source 600 side of the stimulable phosphor sheet 500, as shown in FIG. 38, there exist the subject, front plate 521 of housing 520, and supporting plate 510 (in the order from the radiation source 600), and stimulable phosphor sheet 500 accumulates also the radiation (scattering ray) of the low energy scattered when the radiation passes through them. When the accumulation of the accurate image information is hindered by such the scattering ray, there is a case where various harmful influences such as the lowering of the diagnostic performance are caused.

Particularly, when the subject 700 is arranged above such a radiation image reading apparatus and the radiographing is conducted (that is, in the case of the radiographing at the "lying position"), because it is necessary that a top board 800 supporting the weight of the subject 700 is provided between the subject 700 and the front plate 521 of the housing 520 (refer to FIG. 39), a bad effect in which the scattering ray gives to the radiation image, is larger.

As a means for shielding such the scattering ray, conventionally, a "grid" structured in such a manner that a laminating body in which a radiation absorption layer formed of lead having the high radiation absorption factor and a radiation transmitting layer formed of aluminum, paper, wood, and synthetic resin which have the low radiation absorption factor are alternately provided, is covered by a cover member having the low radiation absorption factor, is used, and the scattering ray is shielded by arranging the grid in the vicinity of the subject 700 side.

However, because there is a case where the radiation is scattered also by a member constituting the grid or grid itself, there is a case where the accurate accumulation and recording of the image information which reaches the stimulable phosphor sheet are hindered.

Further, in the recent years, instead of the radiography system, a radiation image radiographing system by which the radiation detector such as a semiconductor sensor is used and the radiation image is radiographed, the radiation image is converted into the electric signal (image signal), and the electric signal (image signal) is image-processed and displayed on the CRT, is proposed.

A radiation image radiographing apparatus used in the radiation image radiographing system is, generally, provided with the housing fixed at a predetermined position and the radiation detector housed in this housing, and the radiation which is irradiated from the radiation source and passing through the subject and the front plate of the housing, is detected by the radiation detector. The radiation detector is provided with the conversion means for converting the detected radiation into the electric signal (image signal), and the electric signal (image signal) converted corresponding to the level of the detected radiation is sent to the image processing means, and herein, a predetermined image processing is conducted and it is outputted to the image display means such as the CRT, and displayed.

According to the radiation image radiographing system using the radiation image radiographing apparatus, the very broader range radiation can be detected as compared with the radiographing method, and the radiation image with an abundant amount of information can be obtained.

However, the radiation detector housed in the radiation image radiographing apparatus detects even the radiation (scattering ray) of the low energy scattered on each kind of members until the radiation is absorbed in the radiation absorption layer and detected. When the detection of the accurate image signal is hindered by such the scattering ray, there is a case where the various harmful influences such as the lowering of the diagnostic performance are caused.

The object of the present invention is to provide a radiation image radiographing apparatus by which the scattering ray is effectively shielded, and the image quality of the radiation image can be largely increased.

SUMMARY OF THE INVENTION

A radiographing cassette having a housing for housing a stimulable phosphor sheet described in Item 1-1 of the present invention is characterized in that there is provided a scattering radiation shielding grid on the reverse side of a front plate of the housing, and there is provided the stimulable phosphor sheet in contact with the scattered radiation shielding grid.

In the invention described in Item 1-1, since there is provided the grid for shielding the radiation (scattered radiation), having lower leveled energy that is generated when the radiographing is performed, on the reverse side of the front plate of the radiographing cassette, it is possible to prevent image information based on the scattered radiation from being accumulated and recorded on the stimulable phosphor sheet, and further, since the stimulable phosphor sheet is in contact with the grid, image information based on the radiation is accumulated and recorded on the stimulable phosphor sheet, in the step that the scattering of the scattered radiation caused by the grid itself is small, and thereby, it is possible to accumulate and record more correct image information.

The invention described in Item 1-2 is characterized in that the front plate of the above-mentioned housing is formed with a scattering radiation shielding grid, and the stimulable phosphor sheet is provided to be in contact with the reverse side of the front plate, in the radiographing cassette having the housing for housing the stimulable phosphor sheet.

In the invention described in Item 1-2, since the front plate itself of the radiographing cassette is represented by the grid, a primary factor for generating the scattered radiation is less and the scattering radiation is less generated. Further, since the generated radiation is shielded by the grid and the stimulable phosphor sheet is in contact with the grid, image information based on the radiation is accumulated and recorded on the stimulable phosphor sheet, in the step that the scattering of the scattering radiation generated by the grid itself is less, and thereby, it is possible to accumulate and record more correct image information.

The invention described in Item 1-3 is characterized in that the above-mentioned housing is composed of a housing main body having an opening section, the front plate for covering the opening section, and the stimulable phosphor sheet is in contact with the above-mentioned scattered radiation shielding grid, and can be separated from the housing main body together with the front plate, in the radiographing cassette described in Item 1-1 or 1-2.

In the invention described in Item 1-3, since the stimulable phosphor sheet, being in close contact with the grid, is separated from the housing main body, with the front plate, the stimulable phosphor sheet can be supported by the grid, and thereby, it is prevented from being damaged by the case that the stimulable phosphor sheet is bent, when the stimulable phosphor sheet after the radiographing is handled out of the radiographing cassette.

The invention described in Item 1-4 is represented by a radiation image reading apparatus employing the radiographing cassette described in either one of Items 1-1 to 1-3, wherein there are provided, an irradiating means for irradiating exiting light on the surface opposite to the radiation irradiated surface of the above-mentioned stimulable phosphor sheet, and a reading means for reading the above-mentioned radiation image from the stimulable phosphor sheet, by detecting stimulation light generated based on the exiting light irradiated by the irradiating means.

The invention described in Item 1-4 can read image information, accumulated and recorded on the stimulable phosphor sheet, under the condition that the grid is provided and the influence of the scattered radiation is small, on the surface opposite to the radiation-irradiated surface of the stimulable phosphor sheet.

The invention described in Item 1-5 is characterized in that there is provided a stimulable phosphor sheet take-up means which takes up the stimulable phosphor sheet from the radiographing cassette, in the radiation image reading apparatus described in Item 1-4.

Since the invention described in Item 1-5 can take up the stimulable phosphor sheet provided on the grid in the radiographing cassette, the stimulable phosphor sheet after the radiographing can be handled out of the radiographing cassette, and thereby, various means can be employed to read image information.

The invention described in Item 1-6 is represented by a radiation image reading method in the radiation image reading apparatus, described in Item 1-4 or 1-5, wherein exciting light is irradiated on the surface opposite to the surface of the above-mentioned stimulable phosphor sheet where the radiation having used for recording the radiation image is irradiated, and the above-mentioned radiation image can be read from the stimulable phosphor sheet, by the detection of the stimulation light generated based on the exiting light.

The invention described in Item 1-6 can read image information accumulated and recorded on the stimulable phosphor sheet, on the surface opposite to the surface where the radiation is irradiated to the stimulable phosphor sheet, under the condition that the stimulable phosphor sheet is provided on the grid and the influence of the scattered radiation is small.

The invention described in Item 2-1, represented by a radiographing cassette having a housing for housing a stimulable phosphor sheets, is characterized in that there is provided a metallic layer composed of a metal whose atomic number is not less than 20 or an alloy whose effective atomic number is not less than 20, between a front plate of the above-mentioned housing and the stimulable phosphor sheet, and an average radiation transmittance on a local part of 1 mm$^2$ sampled from the surface of the metallic layer optionally is from 1/10 to 10 times that on the total area on the metallic surface, and further the thickness of the metallic layer is in a range of 5 $\mu$m–200 $\mu$m.

In the invention described in Item 2-1, since there is provided the metallic layer that is composed of a specific metallic material and has the specific radiation transmittance and the thickness, between the front plate and the stimulable phosphor sheet, it is possible to shield effectively the radiation (scattered radiation), having low energy, which is scattered when transmitting through the subject. Accordingly, it is possible to improve the image quality of the radiation image remarkably.

The invention described in Item 2-2 is characterized in that an average radiation transmittance on a local part of 1 mm² sampled from the surface of the metallic layer optionally is ½ to 2 times that on the total area on the metallic layer, in the radiographing cassette described in Item 2-1.

The invention described in Item 2-3 is characterized in that the metallic layer is fixed to the reverse side of the front plate, in the radiographing cassette described in Item 2-1 or 2-2.

The invention described in Item 2-4 is characterized in that the metallic layer is composed of at least either one of Cu, Ni, Fe, Pb, Zn, W, Mo, Au, Ag, Ba, Ta, Cd, Ti, Zr, V, Nb, Cr, Co, and Sn, in the radiographing cassette described in Item 2-1, 2-2 or 2-3.

The invention described in Item 2-5 is characterized in that the metallic layer is composed of at least either one of Cu, Ni, Fe, Pb, and Zn, in the radiographing cassette described in Item 2-1, 2-2, or 2-3.

The invention described in Item 2-6 is characterized in that the thickness of the metallic layer is not less than 5 μm and not greater than 50 μm, in the radiographing cassette described in Item 2-1, 2-2, 2-3, 2-4, or 2-5.

The invention described in Item 2-7 is characterized in that the metallic layer has a columnar structure, in the radiographing cassette described in Item 2-1, 2-2, 2-3, 2-4, 2-5, or 2-6.

The invention described in Item 2-8 is characterized in that the metallic layer is produced by an electrolyte method, in the radiographing cassette described in Item 2-1, 2-2, 2-3, 2-4, 2-5, 2-6 or 2-7.

The invention described in Item 2-9 is characterized in that a synthetic resin thin film is laminated on at least one of the surfaces of the metallic layer, in the radiographing cassette described in Item 2-1, 2-2, 2-3, 2-4, 2-5, 2-6, 2-7 or 2-8.

The invention described in Item 2-10 is characterized in that the front plate is a hard one composed of at least either one material of carbon fiber reinforced resin, acrylic resin, phenol resin, polyimide resin, or aluminum, in the radiographing cassette described in Item 2-1, 2-2, 2-3, 2-4, 2-5, 2-6, 2-7, 2-8 or 2-9.

An electronic cassette for radiographic imaging, having a flat type radiation detecting means for detecting the radiation and a flat housing for covering the radiation detecting means, of the invention described in Item 3-1 is characterized in that there is provided a metallic layer composed of a metal whose atomic number is not less than 20 or an alloy whose effective atomic number is not less than 20, between a front plate of the above-mentioned housing and the stimulable phosphor sheet, and an average radiation transmittance on a local part of 1 mm² sampled from the surface of the metallic layer optionally is ⅒ to 10 times that on the total area on the metallic surface, and further the thickness of the metallic layer is not less than 5 μm and not larger than 200 μm.

In the invention described in Item 3-1, since there is provided the metallic layer that is composed of a specific metallic material and has the specific radiation transmittance and the thickness, between the front plate of the housing and the radiation detecting means, it is possible to shield evenly and effectively the radiation (scattering radiation) having low energy. Accordingly, it is possible to improve the image quality of the radiation image remarkably.

The invention described in Item 3-2 is characterized in that an average radiation transmittance on a local part of 1 mm² sampled from the surface of the metallic layer optionally is ½ to 2 times that on the total area on the metallic surface, in the electronic cassette for radiographic imaging described in Item 3-1.

The invention described in Item 3-3 is characterized in that the metallic layer is fixed to the reverse side of the front plate, in the electronic cassette for radiographic imaging described in Item 3-1 or 3-2.

The invention described in Item 3-4 is characterized in that the metallic layer is composed of at least either one of Cu, Ni, Fe, Pb, Zn, W, Mo, Au, Ag, Ba, Ta, Cd, Ti, Zr, V, Nb, Cr, Co, and Sn, in the electronic cassette for radiographic imaging described in Item 3-1, 3-2 or 3-3.

The invention described in Item 3-5 is characterized in that the metallic layer is composed of at least either one of Cu, Ni, Fe, Pb, and Zn, in the electronic cassette for radiographic imaging described in Item 3-1, 3-2, 3-3 or 3-4.

The invention described in Item 3-6 is characterized in that the thickness of the metallic layer is not less than 5 μm and not greater than 50 μm, in the electronic cassette for radiographic imaging described in Item 3-1, 3-2, 3-3, 3-4, or 3-5.

The invention described in Item 3-7 is characterized in that the metallic layer has a columnar structure, in the electronic cassette for radiographic imaging described in Item 3-1, 3-2, 3-3, 3-4, 3-5, or 3-6.

The invention described in Item 3-8 is characterized in that the metallic layer is produced by an electrolyte method, in the electronic cassette for radiographic imaging described in Item 3-1, 3-2, 3-3, 3-4, 3-5, 3-6 or 3-7.

The invention described in Item 3-9 is characterized in that a synthetic resin thin film is coated on at least one of the surfaces of the metallic layer, in the electronic cassette for electronic imaging described in Item 3-1, 3-2, 3-3, 3-4, 3-5, 3-6, 3-7 or 3-8.

The invention described in Item 3-10 is characterized in that the front plate is a hard one made of at least either one material of carbon fiber reinforced resin, acrylic resin, phenol resin, polyimide resin, or aluminum, in the electronic cassette for radiographic imaging described in Item 3-1, 3-2, 3-3, 3-4, 3-5, 3-6, 3-7, 3-8 or 3-9.

The invention described in Item 4-1 is a radiation image reading apparatus, having therein a supporting plate, a stimulable phosphor sheet arranged on the side opposite to the radiation-irradiated side on the supporting plate, and a reading means for reading stimular phosphor light emitted from the stimulable phosphor sheet, in which the stimulable phosphor sheet is irradiated by the radiation, that has passed through the subject and the supporting plate successively, and radiation image information recorded on the stimulable phosphor sheet based on the energy of the irradiated radiation is read, wherein the supporting plate is formed of a scattered radiation shielding grid, and the scattered radiation shielding grid and the stimulable phosphor sheet are provided to be in contact with each other.

In the invention described in Item 4-1, the scattering radiation shielding grid supports and holds the stimulable phosphor sheet, and further prevents the image information, caused by the radiation (scattering radiation) having lower energy generated when the radiographing is performed on the stimulable phosphor sheet, from being accumulated and recorded on the stimulable phosphor sheet. Especially, since the supporting plate is not required by making the grid to be the supporting plate, the scattered radiation generated by the supporting plate is reduced, and the influence of the scattered radiation is further reduced. Further, since the stimulable phosphor sheet is in contact with the grid, image information based on the radiation is accumulated and recorded on the stimulable phosphor sheet, in the stage where scattering of the scattering radiation caused by the grid itself is less, and thereby, it is possible to obtain correct image information by reading the image information accumulated and recorded.

The present invention mentioned in Item 4-2 is characterized in that the stimulable phosphor sheet is coated with a moisture-proof protective film, in the radiation image reading apparatus described in Item 4-1.

Needless to say, the invention described in Item 4-2 can obtain the effect same as the effect of the invention described in Item 4-1, and especially, it is possible to prevent that moisture such as humidity and a stain are stuck to the stimulable phosphor sheet and that a crack is caused on the stimnlable phosphor sheet itself, because the stimulable phosphor sheet is coated by the moisture-proof protective film.

The present invention mentioned in Item 4-3 is characterized in that the scattered radiation shielding grid and the stimulable phosphor sheet are cemented each other through a resin film, in the radiation image reading apparatus described in Item 4-1 or 4-2.

The invention described in Item 4-4 is characterized in that the stimular phosphor light is read from the surface opposite to the surface of the stimulable phosphor sheet irradiated by radiation, in the radiation image reading apparatus described in either one of Items 4-1, 4-2 or 4-3.

The invention described in Item 5-1 is represented by a radiation image reading apparatus, having therein, a supporting plate, a stimulable phosphor sheet arranged at the side opposite to the radiation-irradiated side of the supporting plate, and a reading means for reading a stimulable emission light emitted from the stimulable phosphor sheet, in which the radiation, that has passed through the subject and the supporting plate successively, is irradiated on the stimulable phosphor sheet, and radiation image information, accumulated on the stimulable phosphor sheet based on the energy of the irradiated radiation, is read as the stimular phosphor light wherein there is provided a metallic layer that is composed of a metal whose atomic number is not less than 20 or an alloy whose effective atomic number is not less than 20, at the position that is closer to the subject than from the stimulable phosphor sheet, and an average radiation transmittance on a local part of 1 mm² sampled from the surface of the metallic layer optionally is from 1/10 to 10 times that on the total area on the metallic surface, further the thickness is in a range of 5 μm–200 μm.

In the invention described in Item 5-1, since there is provided a metallic layer that is composed of a specific metallic material and has the specific radiation transmittance and the thickness, at the position that is closer to the subject than the stimulable phosphor sheet, it is possible to shield effectively the radiation (scattered radiation), having low energy, which is scattered when transmitting through the subject. Accordingly, it is possible to improve the image quality of the radiation image remarkably.

The invention described in Item 5-2 is characterized in that a metallic layer is arranged between the supporting plate and the stimulable phosphor sheet, in the radiation image reading apparatus described in Item 5-1.

The invention described in Item 5-3 is characterized in that the stimulable phosphor sheet is fixed to the supporting plate under the condition that the both sides of the stimulable phosphor sheet are coated by a moisture-proof protective film, and the metallic layer is provided in the moisture-proof protective film arranged on the supporting plate side, in the radiation image reading apparatus described in Item 5-1 or 5-2.

The invention described in Item 5-4 is characterized in that an average radiation transmittance on a local part of 1 mm² sampled from the surface of the metallic layer optionally is from ½ to 2 times that on the total area on the metallic surface, in the radiation image reading apparatus described in Item 5-1, 5-2 or 5-3.

The invention described in Item 5-5 is characterized in that the metallic layer is made of at least either one of Cu, Ni, Fe, Pb, Zn, W, Mo, Au, Ag, Ba, Ta, Cd, Ti, Zr, V, Nb, Cr, Co, and Sn, in the radiation image reading apparatus described in Item 5-1, 5-2, 5-3 or 5-4.

The invention described in Item 5-6 is characterized in that the metallic layer is made of at least either one of Cu, Ni, Fe, Pb, and Zn, in the radiation image reading apparatus described in Item 5-1, 5-2, 5-3, or 5-4.

The invention described in Item 5-7 is characterized in that the metallic layer is made of at least either one of Cu, Ni and Fe, in the radiation image reading apparatus described in Item 5-1, 5-2, 5-3, or 5-4.

The invention described in Item 5-8 is characterized in that the thickness of the metallic layer is not less than 5 μm and not greater than 50 μm, in the radiation image reading apparatus described in Item 5-1, 5-2, 5-3, 5-4, 5-5, 5-6 or 5-7.

The invention described in Item 5-9 is characterized in that the metallic layer has a columnar structure, in the radiation image reading apparatus described in Item 5-1, 5-2, 5-3, 5-4, 5-5, 5-6, 5-7 or 5-8.

The invention described in Item 5-10 is characterized in that the metallic layer is produced by an electrolyte method, in the radiation image reading apparatus described in Item 5-1, 5-2, 5-3, 5-4, 5-5, 5-6, 5-7, 5-8 or 5-9.

The invention described in Item 5-11 is characterized in that the front plate is a hard one made of at least either one material of acrylic resin, phenol resin, polyimide resin, carbon fiber reinforced synthetic resin or aluminum, in the radiation image reading apparatus described in Item 5-1, 5-2, 5-3, 5-4, 5-5, 5-6, 5-7, 5-8, 5-9 or 5-10.

The invention described in Item 5-12 is characterized in that the reading means reads the stimulable emission light emitted from the both sides of the stimulable phosphor sheet, in the radiation image reading apparatus described in Item 5-1, 5-2, 5-3, 5-4, 5-5, 5-6, 5-7, 5-8, 5-9, 5-10 or 5-11.

The invention described in Item 6-1 is represented by a radiation image radiographing apparatus having therein a flat type radiation detecting means for detecting the radiation and a housing for covering the radiation detecting means, wherein there is provided a metallic layer made of a metal whose atomic number is not less than 20 or an alloy whose effective atomic number is not less than 20, between the front plate of the above-mentioned housing and the radiation detecting means, and an average radiation transmittance on a local part of 1 mm² sampled from the surface of the metallic layer optionally is from 1/10 to 10 times that on the total area on the metallic surface, and further, the thickness is not less than 5 μm and not greater than 200 μm.

In the invention described in Item 6-1, since there is provided the metallic layer that is made of a specific metallic material and has the specific radiation transmittance and the thickness, between the front plate of the housing and the radiation detecting means, it is possible to shield the radiation (scattered radiation) having low energy, effectively to be in an even condition. Accordingly, it is possible to improve the image quality of the radiation image remarkably.

The invention described in Item 6-2 is characterized in that an average radiation transmittance on a local part of 1 mm$^2$ sampled from the surface of the metallic layer optionally is from ½ to 2 times that on the total area on the metallic surface, in the radiation image radiographing apparatus described in Item 6-1.

The invention described in Item 6-3 is characterized in that the metallic layer is fixed to the reverse side of the front plate, in the radiation image radiographing apparatus described in Item 6-1 or 6-2.

The invention described in Item 6-4 is characterized in that the metallic layer is made of at least either one of Cu, Ni, Fe, Pb, Zn, W, Mo, Au, Ag, Ba, Ta, Cd, Ti, Zr, V, Nb, Cr, Co, and Sn, in the radiation image radiographing apparatus described in Item 6-1, 6-2 or 6-3.

The invention described in Item 6-5 is characterized in that the metallic layer is made of at least either one of Cu, Ni, Fe, Pb, and Zn, in the radiation image radiographing apparatus described in Item 6-1, 6-2, 6-3 or 6-4.

The invention described in Item 6-6 is characterized in that the thickness of the metallic layer is not less than 5 $\mu$m and not greater than 50 $\mu$m, in the radiation image radiographing apparatus described in Item 6-1, 6-2, 6-3, 6-4 or 6-5.

The invention described in Item 6-7 is characterized in that the metallic layer has a columnar structure, in the radiation image radiographing apparatus described in Item 6-1, 6-2, 6-3, 6-4, 6-5, or 6-6.

The invention described in Item 6-8 is characterized in that the metallic layer is produced by an electrolyte method, in the radiation image radiographing apparatus described in Item 6-1, 6-2, 6-3, 6-4, 6-5, 6-6 or 6-7.

The invention described in Item 9-9 is characterized in that a synthetic resin thin film is laminated on at least one of the surfaces of the metallic layer, in the radiation image radiographing apparatus described in Item 6-1, 6-2, 6-3, 6-4, 6-5, 6-6, 6-7 or 6-8.

The invention described in Item 6-10 is characterized in that a front plate is a hard one made of at least either one material of carbon fiber reinforced resin, acrylic resin, phenol resin, polyimide resin, or aluminum, in the radiation image radiographing apparatus described in Item 6-1, 6-2, 6-3, 6-4, 6-5, 6-6, 6-7, 6-8 or 6-9.

BRIEF DESCRIPTION OF THE DRAWINGS

FIG. 20(a) is a conceptual drawing showing a local part of 1 mm$^2$ sampled from the surface of the metallic foil optionally, and FIG. 20(b) is a graph showing an average radiation transmittance in each local part.

FIG. 28(a) is a conceptual drawing showing a local part of 1 mm$^2$ sampled from the surface of the metallic foil optionally, while FIG. 28(b) is a graph showing an average radiation transmittance in each local part.

DETAILED DESCRIPTION OF THE PREFERRED EMBODIMENT

Figure 1:
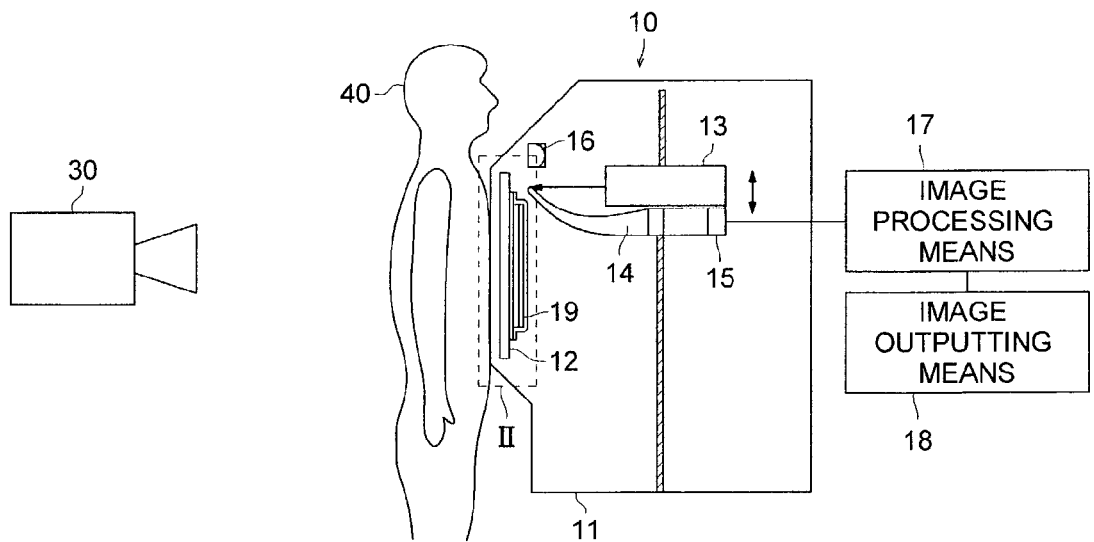
FIG. 1 is a schematic diagram of an X-ray radiation image reading apparatus related to the first embodiment of the present invention.

Referring to the drawings, the embodiments of the present invention will be detailed below. In the present embodiment, an X-ray image reading apparatus (radiation image reading apparatus) used in the "radiation image information recording and reproducing system" by which an X-ray transmitted the subject is irradiated onto the stimulable phosphor sheet, and the image information is accumulated and recorded, will be described.

(The First Embodiment)

Figure 2:
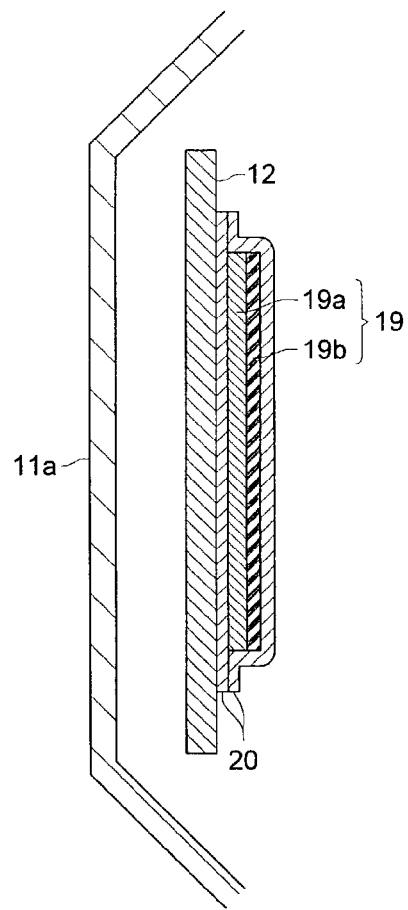
FIG. 2 is an enlarged drawing of part II of FIG. 1.

The X-ray image reading apparatus 10 according to the present embodiment is, as shown in FIG. 1 and FIG. 2, used for the X-ray radiographing at the standing position, and provided with housing 11, grid 12, exciting light source 13, light guiding means 14, photoelectric conversion means 15, erasing means 16, image processing means 17, image output means 18, and stimulable phosphor sheet 19. The exciting light source 13, light guiding means 14, and photoelectric conversion means 15 are arranged on the rear surface side of the stimulable phosphor sheet 19 (opposite side to the X-ray irradiation side), and they structure a reading means for reading the stimulable emission light from the rear surface side of the stimulable phosphor sheet 19.

The housing 11 protects each device mounted in its inside, and together with that, it is a housing which prevents that, after the radiographing, the light is irradiated onto the stimulable phosphor sheet 19 and the accumulated and recorded image information is vanished. In the case of the X-ray radiographing, because it is conducted by irradiating the X-ray which is irradiated from an X-ray source 30 and passes through a subject 40 and the front plate 11a of the housing 11, onto the stimulable phosphor sheet 19, the front plate 11a of the housing 11 is made of the material whose X-ray transmission factor is high. In this connection, in order not to hinder the transmission of the X-ray, it is preferable that the thickness of the front plate 11a is about 1–5 mm. Further, it is preferable that, in order to surely protect an each kind of devices mounted in its inside, the housing 11 is made of the material whose rigidity is comparatively high.

As the material whose X-ray transmission factor is high and rigidity is high, aluminum, carbon fiber reinforced resin, acrylic resin, phenol resin, polyimide resin, and composite material of these resins and aluminum, can be listed. In the present embodiment, as the material of the housing 11, the carbon fiber reinforced resin is adopted.

Figure 3:
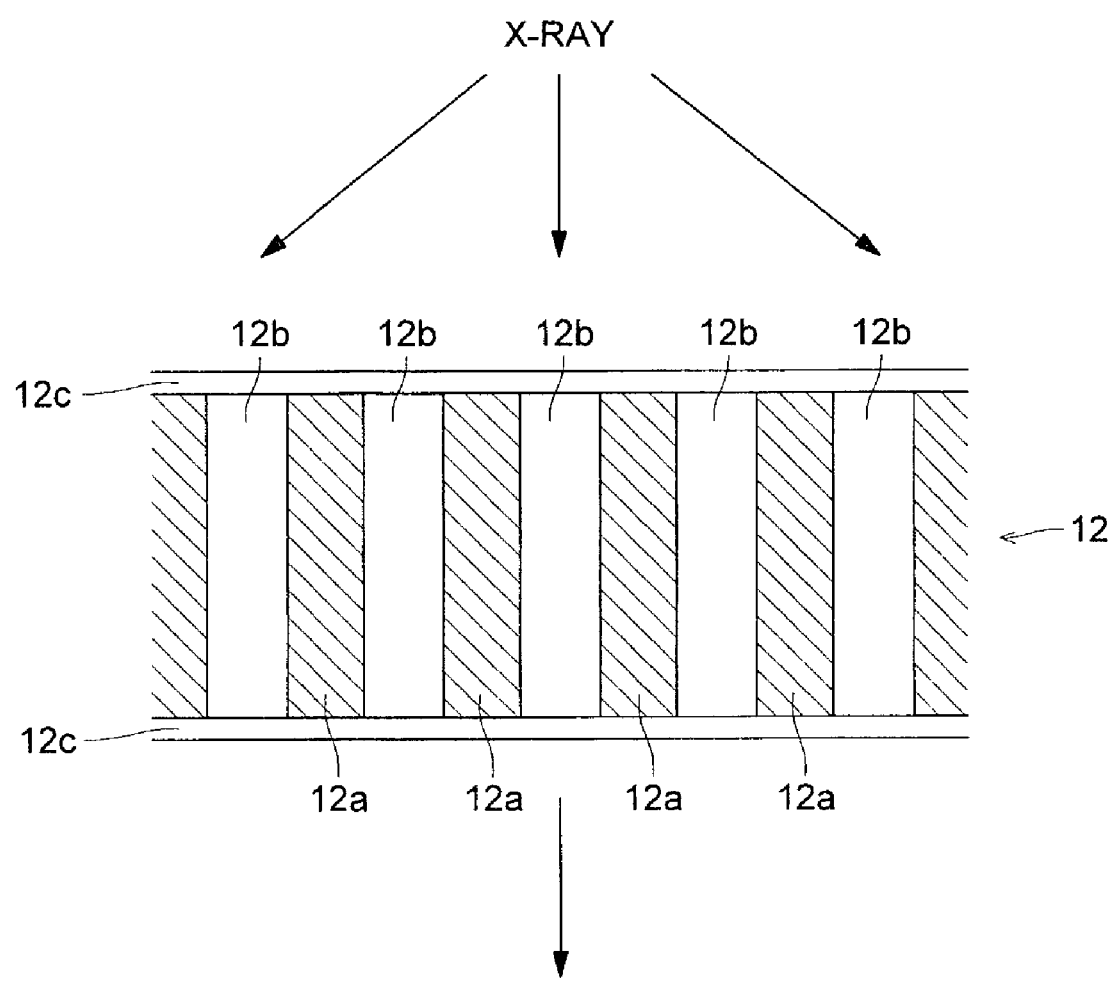
FIG. 3 is an enlarged section of a grid related to the embodiment of the present invention.

The grid 12 is used as a means for shielding the radiation (scattered ray) of the low energy scattered when it passes through the material such as the subject. The grid 12 is, for example, as shown in FIG. 3, structured in such a manner that a lamination body in which the radiation absorption layer 12a formed of lead with the high radiation absorption factor, and the radiation transmission layer 12b formed of aluminum, wood, synthetic resin with the low radiation absorption factor, are alternately provided, is covered by the cover member 12c with the low radiation absorption factor. In the radiation to pass through the grid 12, because the straight advancing component easily passes through, and the scattering ray hardly passes through, as the result, the scattering ray is shielded.

The grid 12 is fixed in the vicinity of the front plate 11a of the housing 11, and also has a function as the supporting body to almost perpendicularly support the stimulable phosphor sheet 19 to the irradiation direction of the X-ray, and in the present embodiment, the stimulable phosphor sheet 19 is fixed on the opposite side surface to the X-ray irradiation side of the grid 12 (refer to FIGS. 1 and 2).

The stimulable phosphor sheet 19 is the sheet in which the stimulable phosphor 19b is laminated on the sheet-like supporting body 19a (refer to FIG. 2). It is preferable that the sheet-like supporting body 19a is, for the operation, made of a material having the flexibility such as wool, cotton, paper, or plastic film. The stimulable phosphor 19b is a material which accumulates the irradiated X-ray energy and, when the exciting light is irradiated, emits the stimulative ray corresponding to the accumulated X-ray energy.

As the stimulable phosphor 19b, rare-earth activated strontium sulfide fluorescent substance, or rare-earth activated lanthanum oxy-sulfide fluorescent substance, disclosed in U.S. Pat. No. 3,859,527, rare-earth activated alkaline earth metal fluoro-halide fluorescent substance, disclosed in U.S. Pat. No. 4,236,078 or Japanese Tokkaihei No. 8-265525, rare-earth activated lanthanum oxy-halide fluorescent substance, disclosed in Japanese Tokkaisho No. 55-12144, copper and/or lead activated zinc sulfide, rare-earth activated alumina.barium oxide or silica.alkaline earth metal oxide fluorescent substance, disclosed in Japanese Tokkaisho No. 55-12142, can be listed.

The stimulable phosphor sheet 19 in the present embodiment is adhered to the grid 12 (through an adhesive agent, not shown) in the situation that its both surfaces are coated by a moisture-proof protective film 20 as a moisture proof-protective film (refer to FIG. 2). The moisture proof protective film 20 performs the function to prevent the water from invading into the stimulable phosphor sheet. It is preferable that this moisture-proof protective film 20 is a film having the high X-ray transmission factor and transparency so that the transmittance of the X-ray, exciting light or stimulable emission light is not prevented.

As the moisture proof protective film 20 having such a characteristic, a resin film such as a polyethylene film, polypropylene film, vinyl chloride resin film, polyethylene terephthalate film, polymethacrylate film, nitrocellulose film, or cellulose acetate film, and their laminated body, and a film in which a thin film such as metal oxide, or silicon nitride is evaporated on these films, can be listed. In the present embodiment, as a moisture-proof protective film 20, a film in which metal oxide is evaporated on the polyethylene terephthalate film, is adopted, and it is arranged on both surfaces of the stimulable phosphor sheet 19, and thermal fusing is conducted on its outside edge.

In this connection, this protective film may also be different on the X-ray irradiation side and exciting light irradiation side, and on the X-ray irradiation side, a very thin metallic thin film which does not prevent the X-ray transmission, can also be used.

The exciting light source 13 performs the function by which the stimulable emission light corresponding to the accumulated and recorded image information, is emitted, by irradiating the exciting light onto the stimulable phosphor sheet 19. The exciting light source 13 in the present embodiment is, by (not shown) drive mechanism, while it is reciprocated in the arrowed direction in FIG. 1, the exciting light can be irradiated onto the stimulable phosphor sheet 19.

The light guiding means 14 functions to guide the stimulable emission light emitted from the stimulable phosphor sheet 19 to the photoelectric conversion means 15, and is made of transparent acrylic plate. In this connection, the light guiding means 14 is reciprocated in timed relationship with the exciting light source 13.

The photoelectric conversion means 15 detects the stimulable emission light emitted from the stimulable phosphor sheet 19, and generates the electric signal corresponding to the light amount of the stimulable emission light. In the present embodiment, as the photoelectric conversion means 15, the photo-multiplier is adopted.

The erasing means 16 functions such that, after the image information is read from the stimulable phosphor sheet 19 by the reading means composed of the exciting light source 13, light guiding means 14 and photoelectric conversion means 15, the radiation energy remaining in this stimulable phosphor sheet 19 is emitted. By this erasing means 16, the new X-ray radiographing can be conducted.

The image processing means 17 obtains the digital image signal by A/D-converting the image information converted into the electric signal by the photoelectric conversion means 15.

The image output means 18 outputs the digital image signal obtained by the image processing means 17 as the X-ray image. As this image output means 18, other than a device displaying the X-ray image such as the CRT or liquid crystal display, a device to produce the hard-copy of the X-ray image, such as an ink jet printer, can be listed.

The image information of the X-ray which passes through the subject 40, front plate 11a and further grid 12, and which is accumulated and recorded on the stimulable phosphor sheet 19, can be read by the X-ray radiographing in the radiation image reading apparatus 10 structured as described above. Particularly, because the grid and the stimulable phosphor sheet are in contact with each other, in the stage in which the scattering of the scattered ray generated by the grid itself is smaller, the image information according to the radiation is accumulated and recorded on the stimulable phosphor sheet, and by reading out the accumulated and recorded information, more accurate image information can be obtained.

Further, as described above, in the opposite surface to the surface on which radiation is irradiated on the stimulable phosphor sheet 19, by reading out the image information, more accurate image information can be obtained.

That is for the reason that the difference is generated in the image information which is accumulated and recorded by the energy difference of the radiation component. The direct component of the image information in the radiation is the radiation with the straight advancing and comparatively high energy. Comparing with that, the scattering ray generated when the radiation collides with the material, is the radiation with comparatively low energy, and the radiation in which the image information is scattered and disturbed. Furthermore, when the grid 12 is provided, the energy of the scattered ray is more reduced.

To accumulate and record the image information on the stimulable phosphor sheet 19, is that the energy of the radiation is absorbed in the stimulable phosphor sheet 19, therefore, the high energy and straight advancing radiation can reach the rear side of the stimulable phosphor sheet 19, and on the rear side, the image information can be accumulated and recorded. On the one hand, in the low energy scattering radiation, although the image information can be accumulated and recorded on the front side of the stimulable phosphor sheet 19, the energy is absorbed before it reaches the rear side, and the component which reaches the rear side is small. Accordingly, because the image information of the rear side is the information in which the direct component of the image information is many (the scattering ray is small), more accurate image information can be obtained.

(The Second Embodiment)

Figure 4:
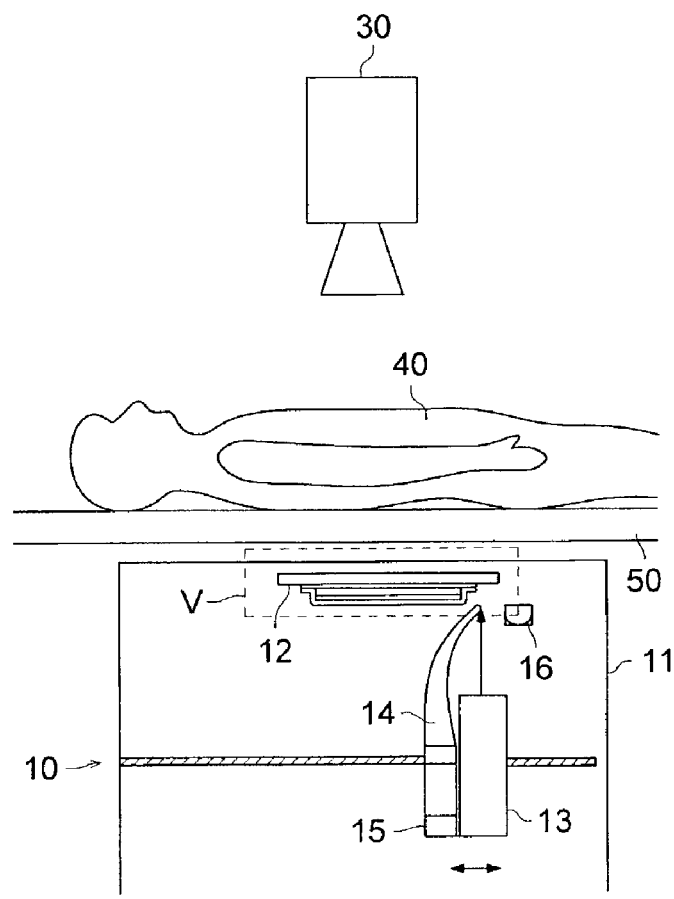
FIG. 4 is a schematic diagram of an X-ray image reading apparatus related to the second embodiment of the present invention.

An X-ray image reading apparatus according to the present embodiment is, as shown in FIG. 4, used for the X-ray radiographing at the lying position, and because the structure and function of the exciting light source 13, reading means composed of the light guiding means 14 and photoelectric conversion means 15, and erasing means 16, and the material characteristic of the housing 11, grid 12, stimulable phosphor sheet 19, and moisture-proof protective film 20, are practically the same as those of the X-ray image reading apparatus according to the first embodiment, the description will be omitted. Further, because the practically same units can be adopted also for the image processing means 17 and image output means 18, the illustration is neglected.

In the present embodiment, above the housing 11 of the X-ray image reading apparatus 10, a top board 50 which supports the weight of the subject 40 is provided (refer to FIG. 4). This top board 50 is structured by the material having the rigidity which can bear the weight of the subject 40 and the high X-ray transmission factor, and in the present embodiment, an acrylic plate is adopted.

By the x-ray radiographing in the thus structured radiation image reading apparatus 10, the image information of the X-ray which passes through the subject 40, top board 50, and front plate 11a and further grid 12, and which is accumulated and recorded on the stimulable phosphor sheet 19, can be read.

Further, in the same as the first embodiment, on the surface opposite to the surface onto which the radiation is irradiated on the stimulable phosphor sheet 19, by reading the image information, more accurate image information can be obtained.

(The Third Embodiment)

Figure 6:
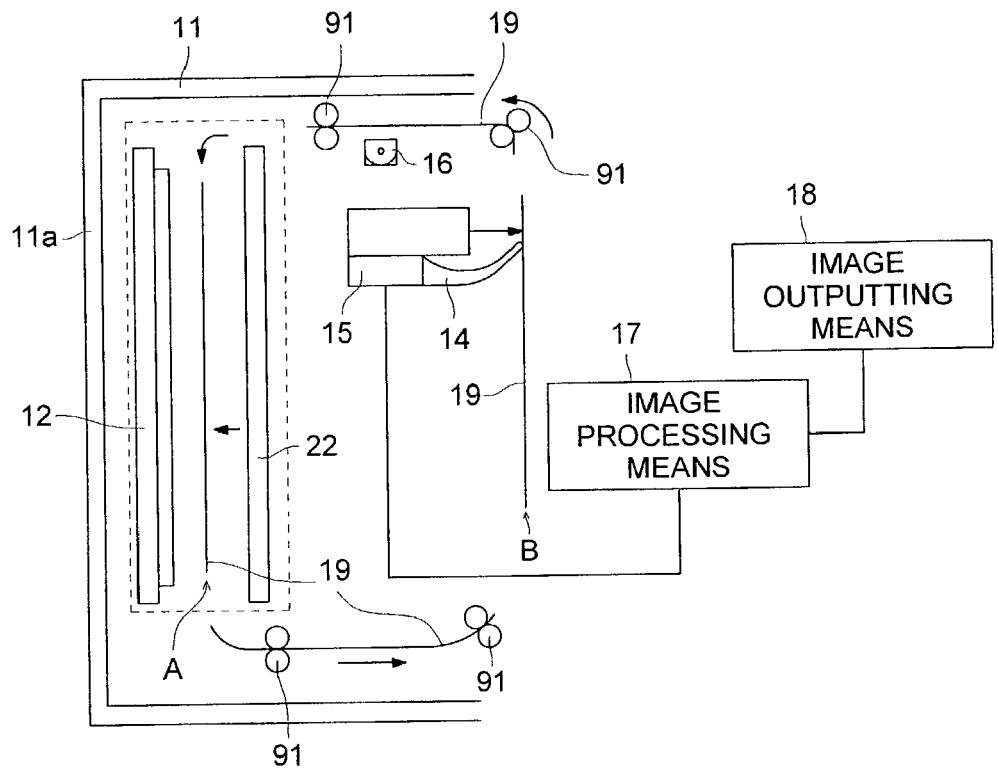
FIG. 6 is a schematic diagram of an X-ray image reading apparatus related to the third embodiment of the present invention.

In the X-ray image reading apparatus relating to the present embodiment, as shown in FIG. 6, the stimulable phosphor sheet 19 is not fixed on the grid 12, and circulated in the apparatus by a circulation conveying means 91, and the image information accumulated on the stimulable phosphor sheet 19 is read out by the reading means provided on a circulation path, and erased by the erasing means 16.

In this connection, in the present embodiment, because the structure and function of the erasing means 16, image processing means 17 and image output means 18, and the material characteristic of the housing 11, grid 12, and stimulable phosphor sheet 19, are practically the same as in the X-ray image reading apparatus according to the first embodiment, the description will be neglected.

In the X-ray image reading apparatus according to the present embodiment, on the rear portion of the grid 12, a pressure plate 22 by which the stimulable phosphor sheet 19 is pushed to the grid 12, and temporarily held, is provided. This pressure plate 22 can be moved in the arrowed direction in FIG. 6 by a drive mechanism, not shown, and the stimulable phosphor sheet 19 conveyed to the radiographing position between the grid 12 and pressure plate 22 can be temporarily held.

Figure 7:
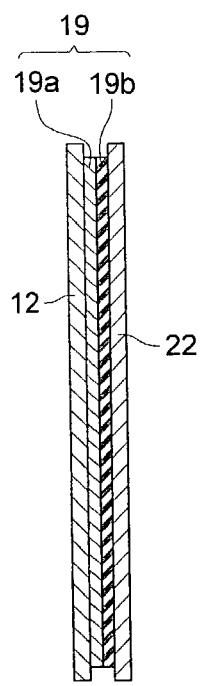
FIG. 7 is an enlarged section of part VII of FIG. 6.

Further, the situation in which, by the grid 12 and pressure plate 22, the stimulable phosphor sheet 19 is held at the radiographic position A, is shown in FIG. 7.

As shown in FIG. 7, after, onto the stimulable phosphor sheet 19 held at the radiographic position A by the grid and pressure plate 22, the X-ray transmitted the subject is irradiated, and the X-ray radiographing is completed, the stimulable phosphor sheet 19 is conveyed to the reading position B by the circulation conveying means 91. In the present embodiment, the light guiding means 14 and photoelectric conversion means 15 are arranged on the rear surface side (opposite side to the X-ray irradiation side) of the stimulable phosphor sheet 19 conveyed to the reading position B (refer to FIG. 6), and the stimulable emission light emitted from the stimulable phosphor sheet 19 can be detected by the exciting light irradiated by the exciting light source 13.

After the image information accumulated on the stimulable phosphor sheet 19 is read at the reading position B, it is conveyed again to the radiographing position A by the circulation conveying means 91. In the present embodiment, because the erasing means 16 is provided on the path on which it is conveyed from the reading position B to the radiographing position A, the radiation energy remaining in the stimulable phosphor sheet 19 is emitted, and it can be used for a new X-ray radiographing.

By the X-ray radiographing in thus structured radiation image reading apparatus, the image information of the X-ray which passes through the subject 40, front plate 11a, and further, grid 12, and which is accumulated and recorded, can be read.

Further, in the same manner as in the first embodiment, on the surface opposite to the surface on which the radiation is irradiated onto the stimulable phosphor sheet 19, by reading the image information, more accurate image information can be obtained. Further, in this correspondence, the image information on the surface on which the radiation is irradiated, can also be read, and the layout of the light guiding means 14 can also be changed.

In this connection, in the embodiments described above, it is structured that an adhesive agent is used when the stimulable phosphor sheet 19 and the grid 12 are adhered, however, the present invention is not limited to this, but, it may also be the adhesion by a double-sided tape. Further, the structure of the radiation reading apparatus is also at will, and for the rest, of course, the specific detailed structure can also be appropriately changed.

Next, an embodiment in which the present invention is applied to a portable cassette type radiation detector, will be described.

(The Fourth Embodiment)

Figure 8:
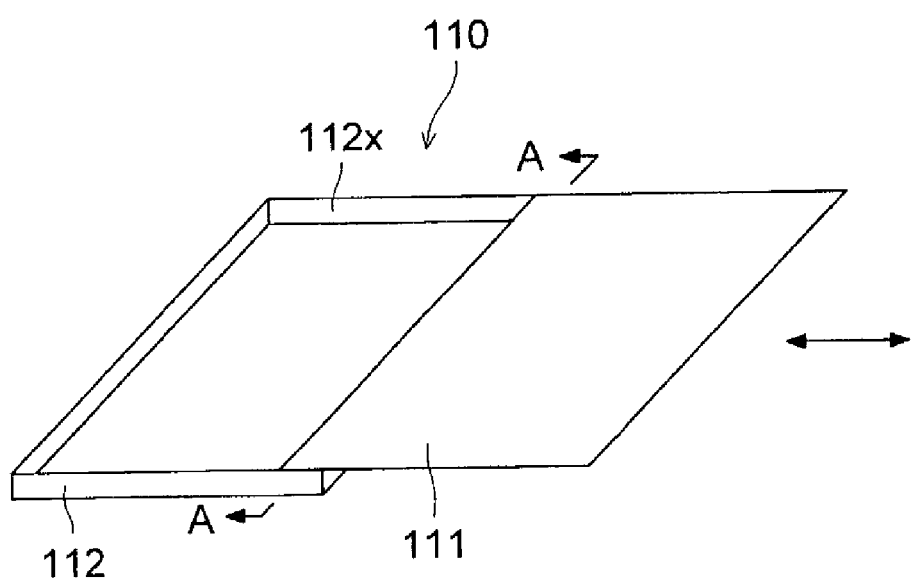
FIG. 8 is a schematic perspective view of a cassette related to the fourth embodiment of the present invention.
Figure 9:
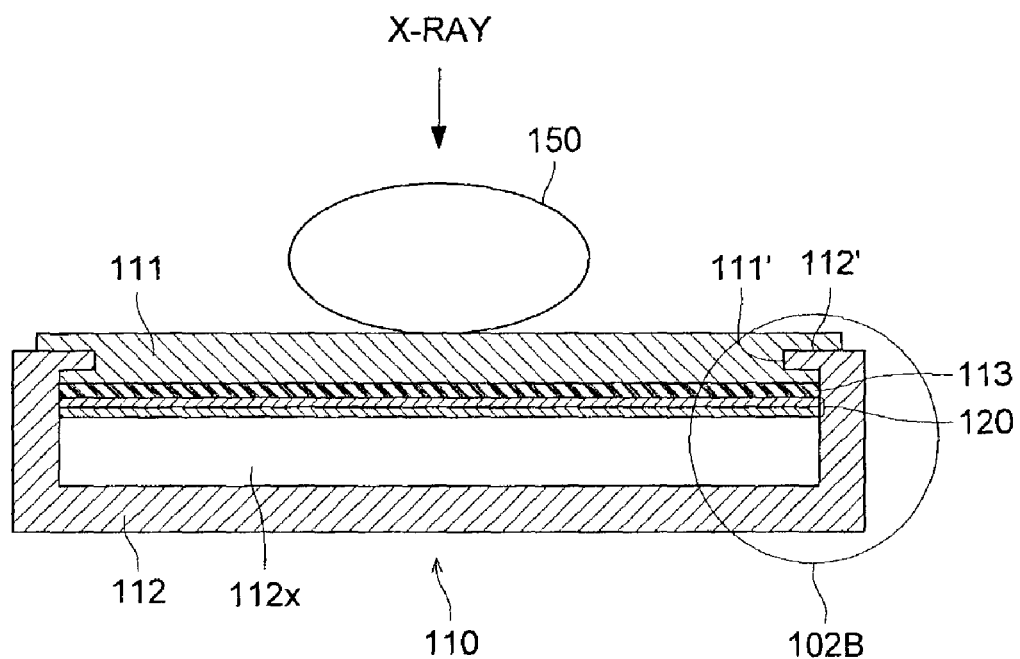
FIG. 9(a) is a section taken on line A—A in FIG. 8.
FIG. 9(b) is an enlarged drawing of part 2B of FIG. 9(a).
Figure 9:
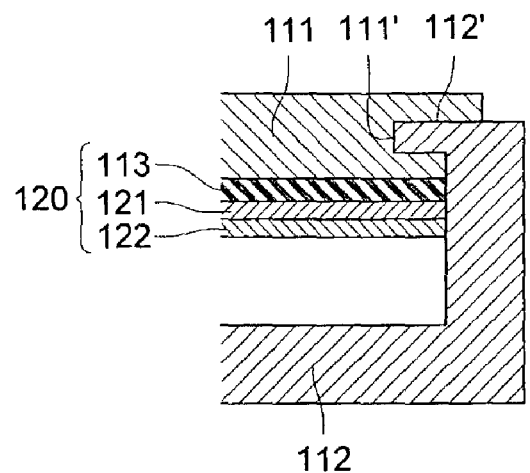
Figure 10:
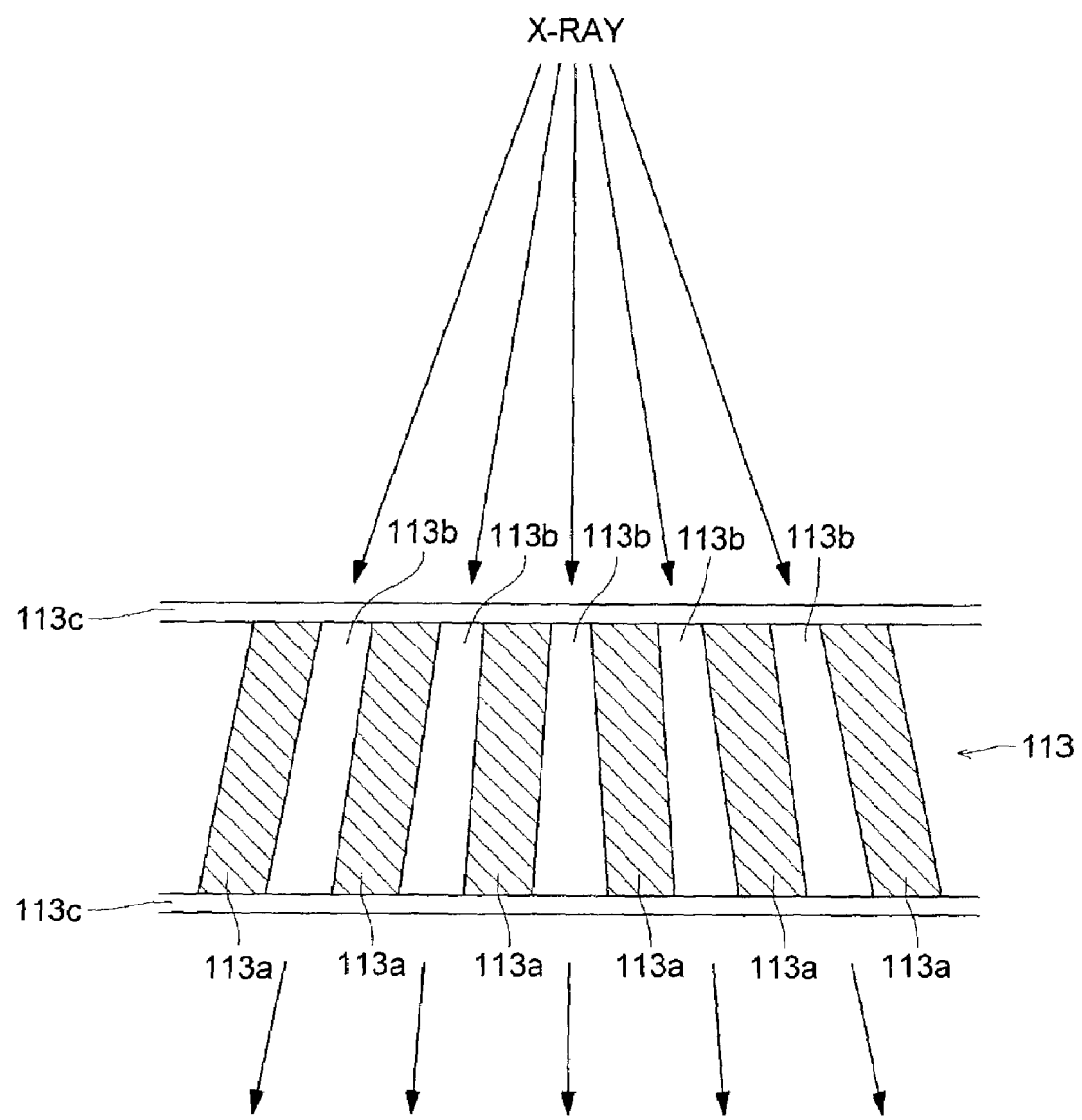
FIG. 10 is an enlarged section of a grid related to the embodiment of the present invention.

A cassette 110 according to the present embodiment is, as shown in FIG. 8, one whose plane shape is rectangular, and the front plate 111 is separably attached from a cassette case 112 as the housing main body. Further, as shown in FIG. 9, the cassette 110 is provided with the front plate 111, grid 113, stimulable phosphor sheet 120, and cassette case 112. The cassette 110 protects the stimulable phosphor sheet 120 at the time of the radiographing or conveying, and after the radiographing, prevents that the light is irradiated on the stimulable phosphor sheet 120 and the accumulated image information is vanished.

On the rear surface of the front plate 111, the grid 113 is provided, and further, on the rear surface of the grid 113, the stimulable phosphor sheet 120 is arranged being in contact with it. This front plate 111 is attached in such a manner that it covers an accommodation portion 112x of the cassette case 112, and after the radiographing, when the light is irradiated on the stimulable phosphor sheet 120, the function as a light shielding plate which prevents the accumulated image information from being vanished, is also performed. In the present embodiment, it is structured in such a manner that, when a guide groove 111' is provided on the side surface of the front plate 111, and a protrusion 112' corresponding to the guide groove 111' is respectively provided in the inside of the side surface of the cassette case 112, the front plate 111 is slid to the cassette case 112 (refer to FIG. 8 and FIG. 9).

The X-ray radiographing is conducted in such a manner that the front plate 111 is attached to the cassette case 112, the stimulable phosphor sheet 120 is accommodated in its accommodation portion 112x, and the X-ray which passes through the subject 150 and front plate 111, and further, grid 113, is irradiated on the stimulable phosphor sheet 120 (refer to FIG. 9(a)). Therefore, the front plate 111 is made of the material whose X-ray transmission factor is high. Further, in order not to hinder the transmission of the X-ray, it is preferable that the thickness of this front plate 111 is about 1–5 mm.

Further, it is preferable that the front plate 111 is made of the material having the high rigidity in order to prevent the physical damage of the stimulable phosphor sheet 120. As the material having the high X-ray transmission factor and high rigidity, aluminum, carbon fiber reinforced resin, acrylic resin, phenol resin, polyimide resin, and composite material of these resins and aluminum, can be listed. In the present embodiment, as the material of the front plate 111, carbon fiber reinforced resin is adopted.

The cassette case 112 is provided with the accommodation portion 112x which accommodates the stimulable phosphor sheet 120, and at the time of radiographing and conveying, prevents the stimulable phosphor sheet 120 from being damaged, and after the radiographing, prevents that, when the light is irradiated on the stimulable phosphor sheet 120, the accumulated and recorded image information is vanished.

As the material of the cassette case 112, when it has the rigidity of the degree in which the physical damage of the stimulable phosphor sheet 120 can be prevented, any material may be used, and each metal, synthetic resin, and fiber reinforced resin can be listed.

The stimulable phosphor sheet 120 in the present embodiment is attached to the front plate 111 (grid 113) by the fixing means, not shown, and following the slide motion of the front plate 111, it is accommodated in, or taken out from the accommodation portion 112x of the cassette case 112 (refer to FIG. 8 and FIG. 9). The thickness of this stimulable phosphor sheet 120 can be appropriately determined corresponding to the accumulated X-ray amount, the kind of the stimulable phosphor, and the height of the accommodation portion 112x of the cassette case 112.

Next, a radiation image reading apparatus using the cassette 110 in the fourth embodiment, and a method will be described.

FIG. 11a shows the main portion structure of the radiation image reading apparatus 180 according to the present embodiment, and it is the apparatus to read the image information accumulated and recorded on the stimulable phosphor sheet 120 accommodated in the cassette 110.

The radiation image reading apparatus 180, as shown in FIG. 11a, is provide with a cassette accommodation portion 180a, image reading section 180b, exciting light source 114 as the irradiating means, light guiding means 115, photoelectric conversion means 116, image processing means 117, image output means 118, and erasing means 119. This radiation image reading apparatus 180 operates in such a manner that it conveys the front plate 111 from the cassette 110 accommodated in the cassette accommodation portion 180a to the image reading section 180b by the conveying means, not shown, next, after, from the stimulable phosphor sheet 120 provided on the front plate 111, the image information is read, it returns the front plate 111 to the cassette case 112.

The exciting light source 114, light guiding means 115, and photoelectric conversion means 116 are arranged on the side of the stimulable phosphor sheet 120 attached to the front plate 111, and particularly the exciting light source 114, light guiding means 115, and photoelectric conversion means 116 structure the reading means for reading the stimulable emission light from the rear surface side (opposite side to the X-ray irradiation side) of the stimulable phosphor sheet 120.

The cassette accommodation portion 180a and image reading portion 180b are units which protect each of devices mounted in their inside, and together with it, prevent the image information in which, after the radiographing, the light is irradiated on the stimulable phosphor sheet 120 and which is accumulated and recorded, from being vanished, and it is preferable that they are made of the materials with comparatively high rigidity, so that they surely protect each of devices mounted in their inside.

The exciting light source 114 performs the function by which, by irradiating the exciting light on the stimulable phosphor sheet 120, the stimulable emission light corresponding to the accumulated and recorded image information is emitted. The exciting light source 114 in the present embodiment, while it is reciprocated in the arrowed direction in FIG. 11a, can irradiate the exciting light on the stimulable phosphor sheet 120.

The light guiding means 115 functions in such a manner that the stimulable emission light emitted from the stimulable phosphor sheet 120 is guided to the photoelectric conversion means 116, and is made of a transparent acrylic plate. In this connection, the light guiding means 115 reciprocates in timed relationship with the exciting light source 114.

The photoelectric conversion means 116 detects the stimulable emission light emitted from the stimulable phosphor sheet 120, and generates the electric signal corresponding to the light amount of the stimulable emission light. In the present embodiment, as the photoelectric conversion means 116, a photo-multiplier is adopted.

The image processing means 117 A/D converts the image information converted into the electric signal by the photoelectric conversion means 116, and obtains the digital signal.

The image output means 118 outputs the digital signal obtained by the image processing means 117 as the X-ray image. As this image output means 118, other than the device displaying the X-ray image such as CRT or liquid crystal display, the device which hardcopies the X-ray image, such as the inkjet printer, can be listed.

After the erasing means 119 reads the image information from the stimulable phosphor sheet 120 by the reading means composed of the exciting light source 114, light guiding means 115, and photoelectric conversion means 116, it emits the radiation energy remaining in the stimulable phosphor sheet 120, and erases the image information. By this erasing means 119, the new X-ray radiographing can be conducted onto the stimulable phosphor sheet 120.

In the radiation image reading apparatus 180 structured in this manner, by the X-ray radiographing using the cassette 110, the image information of the X-ray which passes through the subject 150, and front plate 111, and further, grid 113, and is accumulated and recorded on the stimulable phosphor sheet 120, can be read.

Further, in this manner, on the surface opposite to the surface on which the radiation is irradiated onto the stimulable phosphor sheet 120, by reading the image information, more accurate image information can be obtained.

This is because the difference is generated in the image information accumulated and recorded by the energy difference of the radiation components. The direct component of the image information in the radiation is the radiation having the straight advancing comparatively high energy. As compared with this, the scattering ray generated when the radiation collides with the material, is the radiation having the comparative low energy, and the image information is scattered and disturbed. Furthermore, when the grid 113 is provided, the energy of the scattered ray is more reduced.

Because, to accumulate and record the image information on the stimulable phosphor sheet 120, also means that the energy of the radiation is absorbed in the stimulable phosphor sheet 120, the high energy straight advancing radiation can reach the rear side of the stimulable phosphor sheet 120, and the image information can be accumulated and recorded on the rear side. On the one hand, although the low energy scattered radiation can accumulate and record the image information on the front side of the stimulable phosphor sheet 120, the energy is absorbed before it reaches the rear side, and the component which reaches the rear side is small. Accordingly, because the image information of the rear side is the information which has many direct components of the image information (scattering ray is small), more accurate image information can be obtained.

In this connection, in the fourth embodiment, although the structure in which the grid 113 is provided on the front plate 111, is adopted, the structure in which the front plate 111 itself is formed as the grid 113, may also be adopted. According to this structure, without even the necessity of the structure in which the grid 113 is provided on the front plate 111, the same effect can be obtained.

(The Fifth Embodiment)

Figure 12:
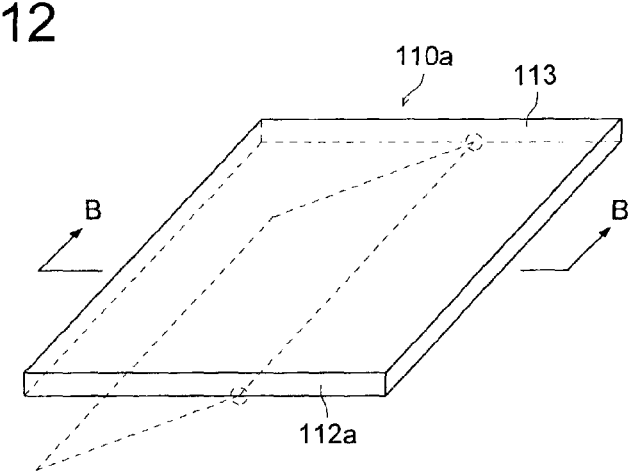
FIG. 12 is a schematic perspective view of a cassette related to the fifth embodiment of the present invention.
Figure 13:
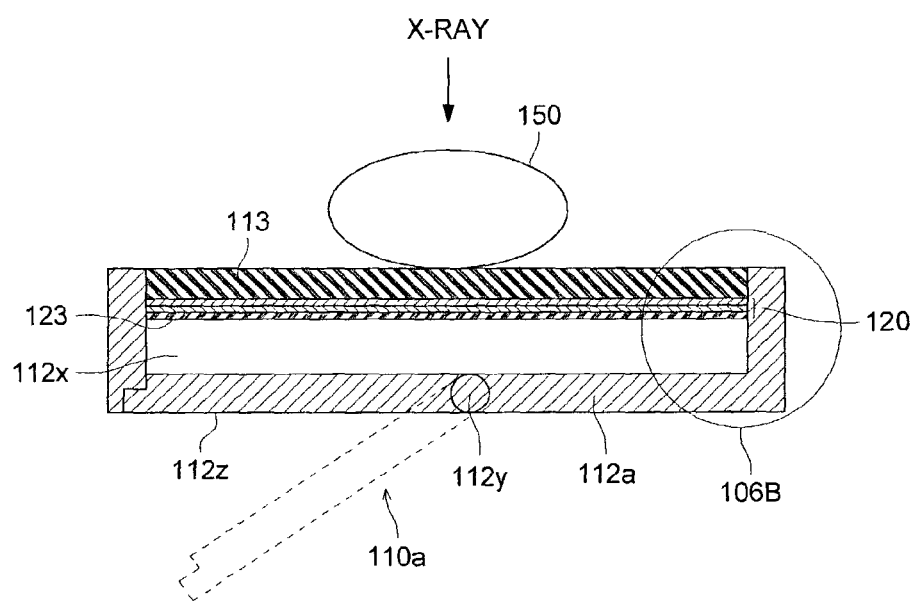
FIG. 13(a) is a section taken on line B—B in FIG. 12.
FIG. 13(b) is an enlarged drawing of part 6B of FIG. 13(a).
Figure 13:
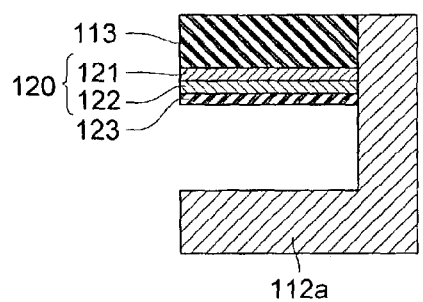

The cassette 110a according to the present embodiment, as shown in FIG. 12, has the rectangular plane shape, and the grid 113 as the front plate is fixed on the cassette case 112a as the housing main body. Further, as shown in FIG. 13, the cassette 110a is provided with the grid 113 as the front plate, stimulable phosphor sheet 120, protective film 123, and cassette case 112a. This cassette 110a protects the stimulable phosphor sheet 120 at the time of radiographing or conveying, and further, prevents the image information in which the light is irradiated on the stimulable phosphor sheet 120 after the radiographing, from being vanished.

The grid 113 as the front plate is provided with the stimulable phosphor sheet 120, and attached so as to cover the accommodation portion 112x of the cassette case 112a, and also performs the function as the light shielding plate which, after the radiographing, when the light is irradiated on the stimulable phosphor sheet 120, prevents the case where the accumulated image information is vanished. In the present embodiment, the grid 113 as the front plate and the cassette case 112a are the fixedly provided integrated structure (refer to FIG. 12, FIG. 13a and FIG. 13b).

Relating to the X-ray radiographing, because it is the same as the fourth embodiment, the description will be omitted.

The cassette case 112a is provided with the accommodation portion 112x to accommodate the stimulable phosphor sheet 120, and prevents, at the time of the radiographing or conveying, the stimulable phosphor sheet 120 from being damaged, and together with that, prevents, when the light is irradiated on the stimulable phosphor sheet 120 after the radiographing, the accumulated and recorded image information from being vanished.

Further, on the cassette case 112a, a rotation axis 112y, and an open and close-able lid portion 112z which is attached to the rotation axis 112y and rotated around the rotation axis 112y as the center, are provided.

The lid portion 112z is opened in the case where the stimulable phosphor sheet 120 is taken from the cassette case 112a when the image information accumulated and recorded on the stimulable phosphor sheet 120 is read, in the radiation image reading apparatus inside.

In this connection, in FIGS. 12, 13a and 13b, the rotation axis 112y is provided at about the center of the cassette case 112a, however, when it is a portion where the aperture area from which the stimulable phosphor sheet 120 can be taken from the cassette case 112a can be secured, it is not particularly limited, and further, corresponding to a portion at which the rotation axis 112y is provided, the dimension of the lid portion 112z is changed.

In this connection, because the material of the cassette case 112a is the same as the cassette case 112, the description will be omitted.

Relating to the grid 113, because it is the same as the fourth embodiment, the description will be omitted.

The protective film 123 having the light transparency is provided on the surface of the stimulable phosphor 122 of the stimulable phosphor sheet 120 (sheet-like supporting body 121, the stimulable phosphor 122), and prevents the deterioration and damage of the stimulable phosphor 122. In this connection, the sheet-like supporting body 121 and protective film 123 in the fifth embodiment are structured by the material having particularly the flexibility, for example, such as PET.

The stimulable phosphor sheet 120 in the present embodiment is attached to the grid 113 as the front plate by a fixing means, not shown, and is accommodated in the accommodation portion 112x of the cassette case 112a (refer to FIGS. 13a and 13b). The thickness of the stimulable phosphor sheet 120 can be appropriately determined corresponding to the accumulating X-ray amount, the kind of the stimulable phosphor, and the height of the accommodation portion 112x of the cassette case 112a.

Next, the radiation image reading apparatus using the cassette 110a of the fifth embodiment and the method will be described.

Figure 14:
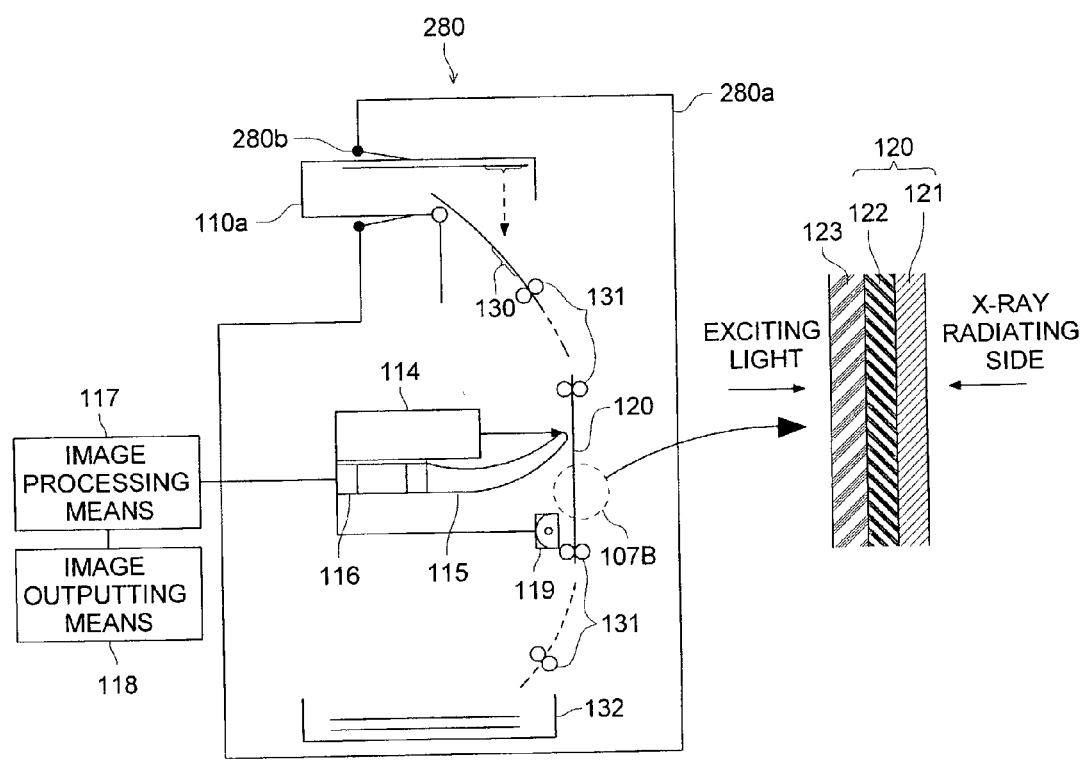
FIG. 14(a) is a schematic diagram of a radiation image reading apparatus related to the fifth embodiment of the present invention.
FIG. 14(b) is an enlarged drawing of part 107B of FIG. 14(a).

FIG. 14a is a view showing the main portion structure of the radiation image reading apparatus 280 according to the present embodiment, and it is an apparatus to read the image information accumulated and recorded on the stimulable phosphor sheet 120 accommodated in the cassette 110a.

The radiation image reading apparatus 280 is, as shown in FIG. 14a, provided with an apparatus housing 280a, cassette insertion portion 280b, the exciting light source 114, light guiding means 115, photoelectric conversion means 116, image processing means 117, image output means 118, erasing means 119, a stimulable phosphor sheet take-out means 130, stimulable phosphor sheet conveying means 131, and stimulable phosphor sheet accommodation portion 132.

The radiation reading apparatus 280 operates in such a manner that the lid portion 112z of the cassette 110a which is inserted into the cassette insertion portion 280b of the apparatus housing 280a is opened, and from the opening section, the image information is read by the reading means (exciting light source 114, light guiding means 115, photoelectric conversion means 116) which is provided on the conveying path on which the stimulable phosphor sheet 120 taken out by the stimulable phosphor sheet take-out means 130 is conveyed by the stimulable phosphor sheet conveying means 131.

The exciting light source 114, light guiding means 115, and photoelectric conversion means 116 are arranged on the rear surface side (opposite side to the X-ray irradiation side) of the stimulable phosphor sheet 120 conveyed by the stimulable phosphor sheet conveying means 131, and they structure the reading means for reading the stimulable emission light from the rear surface side of the stimulable phosphor sheet 120.

The apparatus housing 280a protects each kind of devices mounted in its inside, and together with this, prevents the image information in which the light is irradiated on the stimulable phosphor sheet 120 after the radiographing, and accumulated and recorded, from being vanished, and it is preferable that it is made of the material having the comparatively high rigidity so that each kind of devices mounted in its inside can be surely protected.

The aperture of the cassette insertion portion 280b is simultaneously opened with the insertion of the cassette 110a. At the time of the opening, by the structure in which the opening section is closely contact with the cassette 110a, it is structured so that the light does not enter the inside of the apparatus housing 280a.

Although it is only different from the first embodiment that the exciting light source 114, light guiding means 115, and photoelectric conversion means 116 are not moved by the drive mechanism, because other functions are same, the description will be omitted. Further, because the image processing means 117 and image output means 118 are the same as the fourth embodiment, the description will be omitted.

The stimulable phosphor sheet take-out means 130 is a means by which the stimulable phosphor sheet 120 is taken from the inside of the cassette 110a by, for example, a suction cup, and guided to the stimulable phosphor sheet conveying means 131.

The stimulable phosphor sheet conveying means 131 is a means by which the stimulable phosphor sheet 120 is conveyed by, for example, one pair of the upper and lower guide rollers to the position at which the image information is read by the reading means (the exciting light source 114, light guiding means 115, and photoelectric conversion means 116). The sheet-like supporting body 121 and protective film 123 of the stimulable phosphor sheet 120 are structured by the material having the flexibility, therefore, at the time of the conveyance by the guide roller, even when it is not only the straight advancing conveying path, but also the arc-like curving conveying path, the stimulable phosphor sheet 120 can be conveyed.

Further, in the stimulable phosphor sheet 120 by which the reading of the image information is completed, the radiation energy remaining in the stimulable phosphor sheet 120 is discharged by the erasing means 119, and the image information is erased. By this erasing means 119, after the stimulable phosphor sheet 120 becomes the situation in which the new X-ray radiographing can be conducted, it is conveyed to the stimulable phosphor sheet accommodation portion 132.

The stimulable phosphor sheet accommodation portion 132 accommodates the stimulable phosphor sheet 120 in which the reading of the image information is completed. The accommodated stimulable phosphor sheet 120 is taken out by a predetermined method.

In the radiation reading apparatus 280 structured in this manner, by the X-ray radiographing using the cassette 110a, the image information of the X-ray which passes through the subject 150 and grid 113, and which is accumulated and recorded on the stimulable phosphor sheet 120, can be read.

Further, in the same as in the first embodiment, on the surface opposite to the surface on which the radiation is irradiated on the stimulable phosphor sheet 120, when the image information is read, more accurate image information can be obtained.

Further, a modified example of the radiation image reading apparatus using the cassette 110a of the fifth embodiment, will be described.

FIG. 15a shows the main portion structure of the radiation image reading apparatus 280' according to the present embodiment, and it is an apparatus by which, after the stimulable phosphor sheet 120 accommodated in the cassette 110a is taken out, and the image information accumulated and recorded on the stimulable phosphor sheet 120 is read out, the operation to return the stimulable phosphor sheet 120 to the cassette 110a, is conducted.

Figure 15:
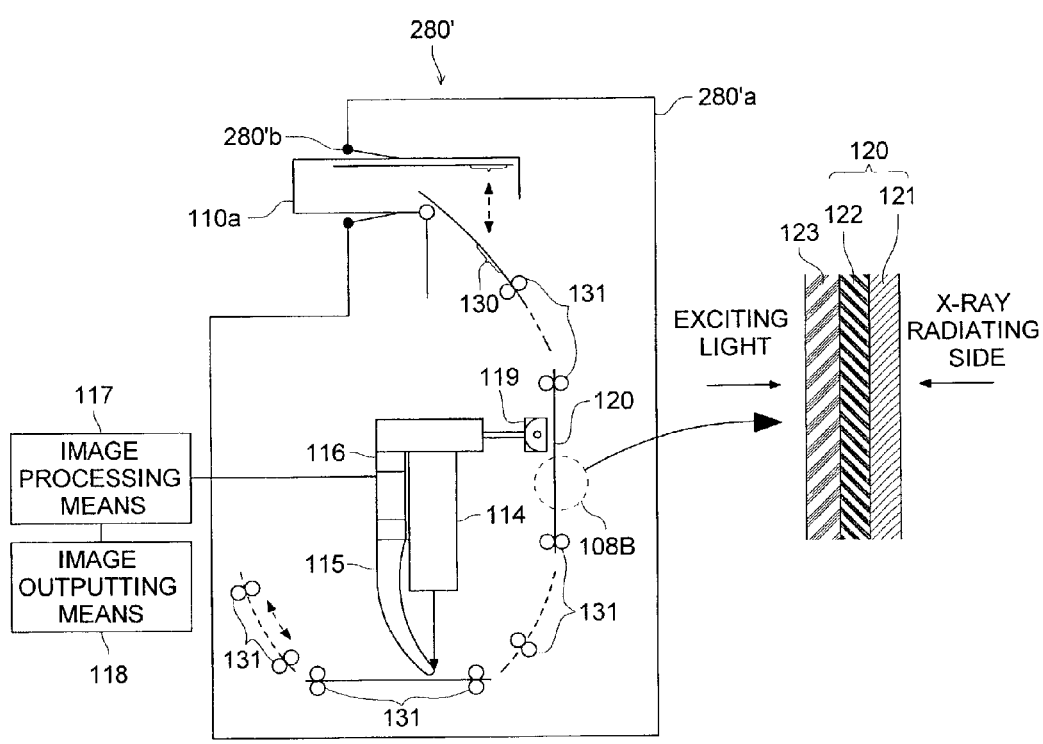
FIG. 15(a) is a schematic diagram of a variation of a radiation image reading apparatus related to the fifth embodiment of the present invention.
FIG. 15(b) is an enlarged drawing of part 108B of FIG. 15(a).

The radiation image reading apparatus 280' is, as shown in FIG. 15, provided with an apparatus housing 280'a, cassette insertion portion 280'b, the exciting light source 114, light guiding means 115, photoelectric conversion means 116, image processing means 117, image output means 118, erasing means 119, stimulable phosphor sheet take-out means 130, and stimulable phosphor sheet conveying means 131.

In the radiation image reading means 280', as compared with the radiation image reading apparatus 280, only the conveying path of the stimulable phosphor sheet 120 is different, and because the other functions are same, only the different portion will be described.

The stimulable phosphor sheet 120 taken from the inside of the cassette 110a by the stimulable phosphor sheet take-out means 130, is guided by the stimulable phosphor sheet conveying means 131 to the position of the reading means (the exciting light source 114, light guiding means 115, and photoelectric conversion means 116), and the image information is read out. The sheet-like supporting body 121 and protective film 123 of the stimulable phosphor sheet 120 are structured by the material having the flexibility, therefore, at the time of the conveyance by the guide roller, even when it is not only the straight advancing conveying path, but also the arc-like curving conveying path, the stimulable phosphor sheet 120 can be conveyed. In the stimulable phosphor sheet 120 by which the reading of the image information is completed, the radiation energy remaining in the stimulable phosphor sheet 120 is discharged by the erasing means 119 provided on the conveying path on which it is returned to the cassette 110a by the stimulable phosphor sheet conveying means 131, and the image information is erased. By this erasing means 119, after the stimulable phosphor sheet 120 becomes the situation in which the new X-ray radiographing can be conducted, it is returned to the inside of the cassette 110a by the stimulable phosphor sheet conveying means 131.

Even when the apparatus is the radiation image reading apparatus 280' of such structure, the same effect as the radiation image reading apparatus 280 is obtained.

In this connection, in the fifth embodiment, the structure in which the grid 113 as the front plate is provided, is adopted, however, the structure in which the front plate is provided on the outer surface of the grid 113 as a separated body, may also be adopted. According to such a structure, the cassette 110a can be reinforced by the front plate, and together with that, the same effect can be obtained.

In this connection, the protective film 123 is not necessary when the stimulable phosphor 122 is not deteriorated or damaged, or when the deterioration or damage is not problem, and it may be not provided.

(The Sixth Embodiment)

Figure 16:
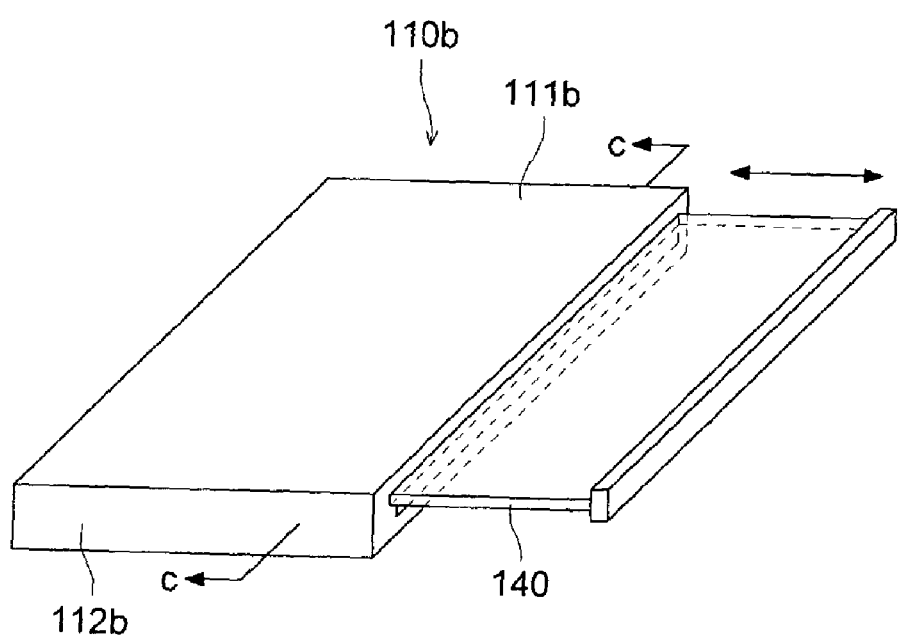
FIG. 16 is a schematic perspective view of a cassette related to the sixth embodiment of the present invention.
Figure 17:
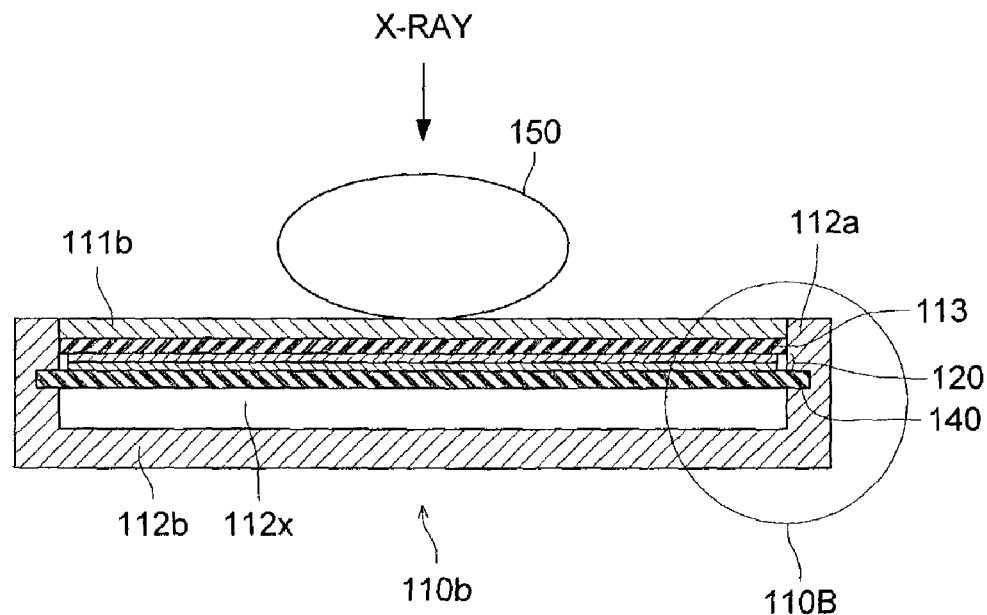
FIG. 17(a) is a section taken on line C—C in FIG. 16.
FIG. 17(b) is an enlarged drawing of part 110B of FIG. 17(a).
Figure 17:
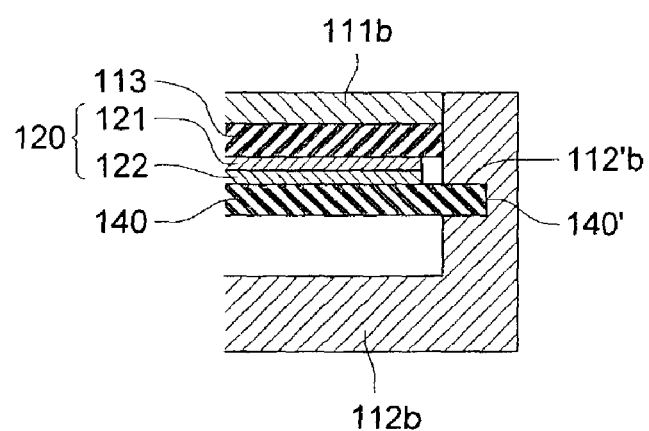

The cassette 110b according to the present embodiment, as shown in FIG. 16, has the rectangular plane shape, and the slide plate 140 is separably jointed with the cassette case 112b. Further, as shown in FIGS. 17a and 17b, the cassette 110b is provided with the front plate 111b, grid 113, stimulable phosphor sheet 120, slide plate 140, and cassette case 112b. This cassette 110b protects the stimulable phosphor sheet 120 at the time of radiographing or conveying, and together with this, prevents the image information in which the light is irradiated on the stimulable phosphor sheet 120 after the radiographing and accumulated, from being vanished.

The grid 113 is attached to the rear surface of the front plate 111b. The front plate 111b is attached so as to cover the accommodation portion 112x of the cassette case 112b, and when the light is irradiated on the stimulable phosphor sheet 120 after the radiographing, it also performs the function as the light shielding plate to prevent the accumulated image information from being vanished.

Relating the X-ray radiographing, because it is the same as the forth embodiment, the description will be omitted. Further, relating to the front surface 111b, because its material is the same as the front plate 111, the description will be omitted.

In the cassette case 112b, other than a point that its shape is different from the cassette case 112, because it is the same, the description will be omitted. Further, because the grid 113 is the same as the fourth embodiment, the description will be omitted.

The slide plate 140 is formed of the resins having the light transparency, and to its surface side (the X-ray irradiation side), the stimulable phosphor sheet 120 is attached. In the present invention, it is structured such that, when the a side edge portion 140' of the slide plate 140 is engaged with a guide groove 112'b corresponding to the thickness of the side edge portion 140', that is, with the inside of the side surface of the cassette case 112, the slide plate 140 is slid to the cassette case 112b (refer to FIG. 16, FIG. 17a and FIG. 17b).

Because the stimulable phosphor sheet 120 (sheet-like supporting body 121, stimulable phosphor 122) is the same as the fourth embodiment, the description will be omitted.

Figure 11:
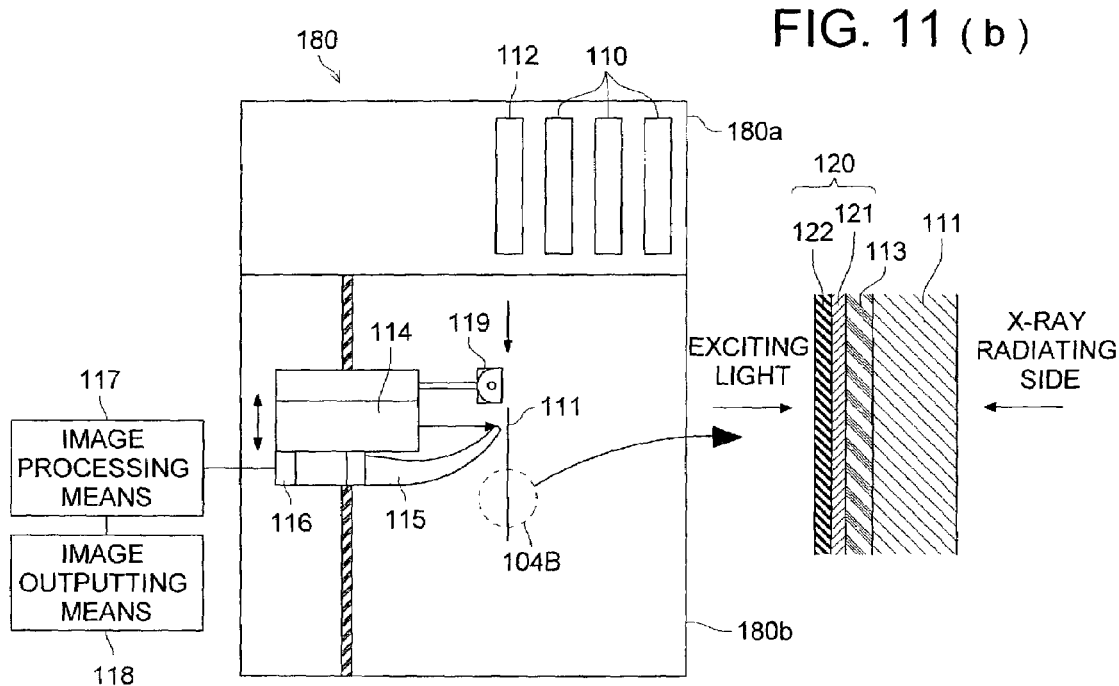
FIG. 11(a) is a schematic diagram of a radiation image reading apparatus related to the fourth embodiment of the present invention.
FIG. 11(b) is an enlarged drawing of part 104B of FIG. 11(a).

The stimulable phosphor sheet 120 in the present invention is attached to the slide plate 140 by the fixing means, not shown, and following the slide operation of the slide plate 40, it is accommodated in or taken from the accommodation portion 112x of the cassette case 112b (refer to FIG. 11, FIG. 17a and FIG. 17b). In this case, because the grid 113 and the stimulable phosphor sheet 120 are in the condition of close contact with each other, there is a possibility that the friction is generated between the grid 113 and the stimulable phosphor sheet 120 at the time of the slide operation. Therefore, it is preferable that the stimulable phosphor sheet 120 is protected by covering with the protective film (not shown). By the protection, the stimulable phosphor sheet 120 is prevented from the flaws being generated by the friction, and the deterioration of the image information due to the flaws is prevented.

The thickness of the stimulable phosphor sheet 120 can be appropriately determined corresponding to the accumulated X-ray amount, the kind of the stimulable phosphor, and the height of the accommodation portion 112x of the cassette case 112b.

Next, the radiation image reading apparatus using the cassette 110b of the sixth embodiment, and the method will be described.

Figure 18:
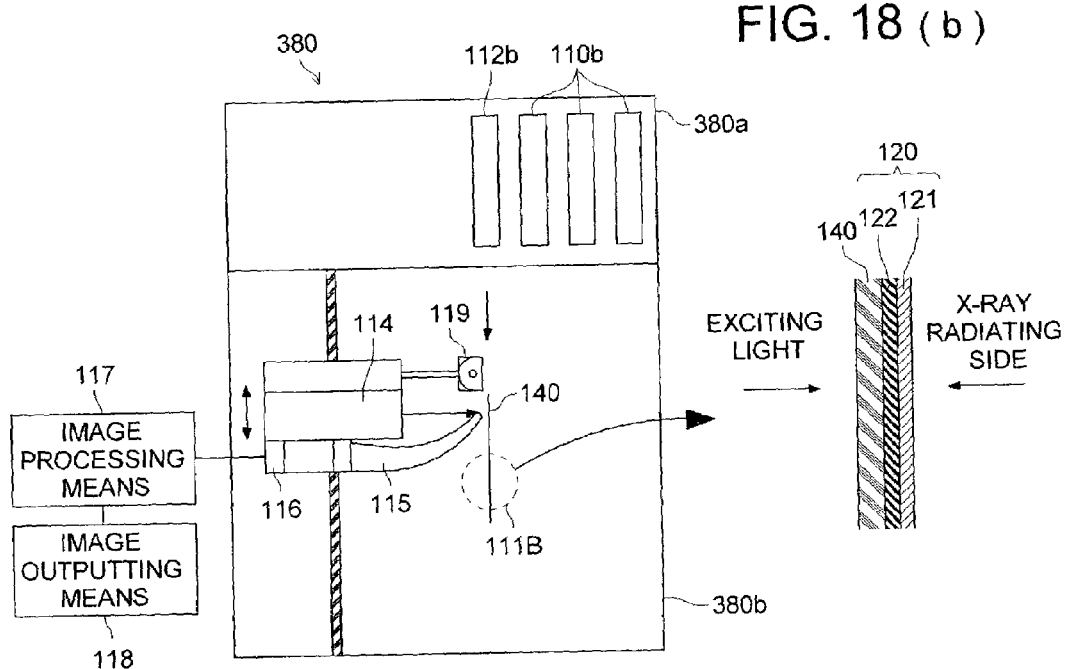
FIG. 18(a) is a schematic diagram of a radiation image reading apparatus related to the sixth embodiment of the present invention.
FIG. 18(b) is an enlarged drawing of part 111B of FIG. 18(a).

FIG. 18a is a view showing the main portion structure of the radiation image reading apparatus 380 according to the present embodiment, and it is an apparatus to read the image information accumulated and recorded on the stimulable phosphor sheet 120 accommodated in the cassette 110b.

The radiation image reading apparatus 380 is, as shown in FIG. 18a, provided with a cassette accommodation portion 380a, the exciting light source 114, light guiding means 115, photoelectric conversion means 116, image processing means 117, image output means 118, and erasing means 119.

The radiation reading apparatus 380 operates in such a manner that, from the cassette 110b accommodated in the cassette accommodation portion 380a, the slide plate 140 is conveyed to the image reading section 380b by the conveying means, not shown, and next, after the image information is read from the stimulable phosphor sheet 120 provided on the slide plate 140, the slide plate 140 is returned to the cassette case 112b.

The exciting light source 114, light guiding means 115, and photoelectric conversion means 116 are arranged on the slide plate 140 side, and they structure the reading means for reading the stimulable emission light from the rear surface side (opposite side to the X-ray irradiation side) of the stimulable phosphor sheet 120.

In the radiation image reading apparatus 380, other than a point that the slide plate 140 is conveyed from the cassette 110b to the image reading section 380b by the conveying means, not shown, and the image information is read, because it is the same as the fourth embodiment (radiation reading apparatus 180), the description will be omitted.

According to the radiation image reading apparatus 380 structured as described above, by the X-ray radiographing using the cassette 110b, the image information of the X-ray which passes through the subject 150 and front plate 111b, and further, grid 113, and which is accumulated and recorded on the stimulable phosphor sheet 120, can be read. Particularly, because the slide plate 140 has the light penetrability, the image information accumulated and recorded on the stimulable phosphor sheet 120 can be read through the slide plate 140.

Further, in the same as the fourth embodiment, on the surface opposite to the surface on which the radiation is irradiated onto the stimulable phosphor sheet 120, by reading the image information, more accurate image information can be obtained.

Further, the slide plate 140 functions also as the protective plate to protect the stimulable phosphor 122 of the stimulable phosphor sheet 120.

As described above, in the cassette, when the radiation image accumulated and recorded on the stimulable phosphor sheet 120 provided in contact with the grid 113 is read from the stimulable phosphor sheet 120, on the surface opposite to the surface on which the radiation is irradiated onto the stimulable phosphor sheet 120, when the image information is read, more accurate image information can be obtained.

In this connection, in the above embodiments, it is defined that the front plates 111 and 111b are made of the carbon fiber reinforced resins, however, the present invention is not limited to this, but it may also be made of the grid, and further, it may also be structured such that, on the front surface of the grid 113, the front plate is provided.

Further, it is defined that the front plate 111 is detachable by the slide motion, however, the present invention is not limited to this, but any detaching mechanism by using the holding means or engaging means may also be used. Further, the structure of the radiation image reading apparatus is also at will, and other than that, it is of course that also the specific detailed structure is appropriately changeable.

(The Seventh Embodiment)

Instead of the grid in the first to the sixth embodiments, an embodiment using a metallic foil (used as a metallic layer) will be described below.

Figure 19:
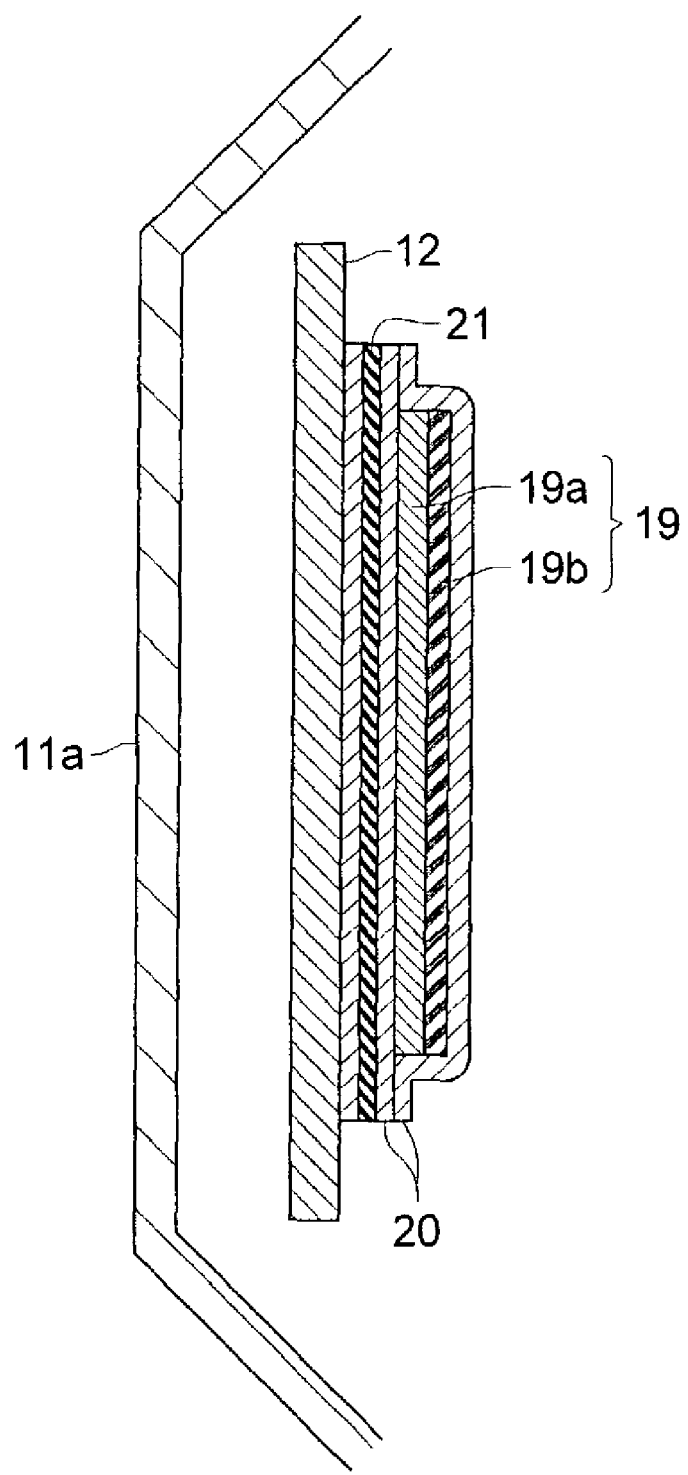
FIG. 19 is an example in which metallic foil is employed instead of a grid in FIG. 2 in the seventh embodiment of the present invention.

FIG. 19 is an example in which the metallic foil is used instead of the grid in FIG. 2, and in the moisture-proof protective film 20 arranged on the supporting plate 12 side, a metallic foil 21 is provided. This metallic foil 21 is a metallic layer which performs the function to remove the X-ray (scattered ray) of the low energy scatted when the X-ray successively passes through the subject 140, front plate 11a of the housing 11 and supporting plate 12.

In order to perform the above-described function, the metallic foil 21 is structured by a metal more than the atomic number 20, or an alloy more than the effective atomic number 20. For example, it can be structured by at least one kind in the metals more than the atomic number 20 such as Cu, Ni, Fe, Pb, Zn, W, Mo, Au, Ag, Ba, Ta, Cd, Ti, Zr, V, Nb, Cr, Co and Sn, or an alloy of these metals. Because these metals and alloys absorb the low energy X-ray, the scattered ray can be effectively absorbed and removed.

Herein, the "effective atomic number" means the atomic number when the atomic number of each metal constituting the alloys is averaged based on the mole ratio. For example, in the case of an alloy structured in the condition that the mole ratio of Co (the atomic number 27) and Cu (the atomic number 29) is 1:1, the effective atomic number is 28. In the present embodiment, as the metallic foil 21, the copper foil structured by Cu (the atomic number is 29) is adopted.

Figure 20:
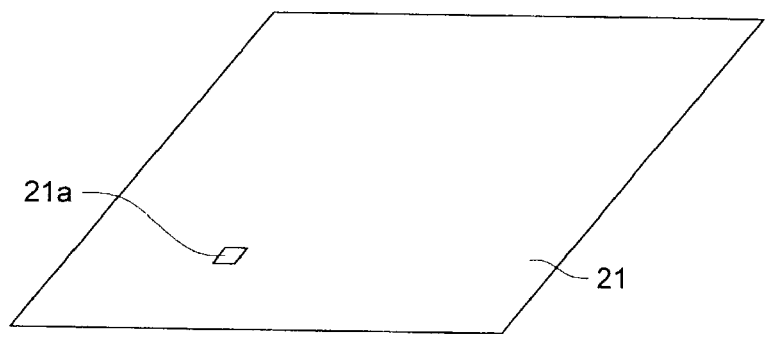
FIGS. 20(a) and 20(b) are for the purpose of explaining radiation transmittance for metallic foil.
Figure 20:
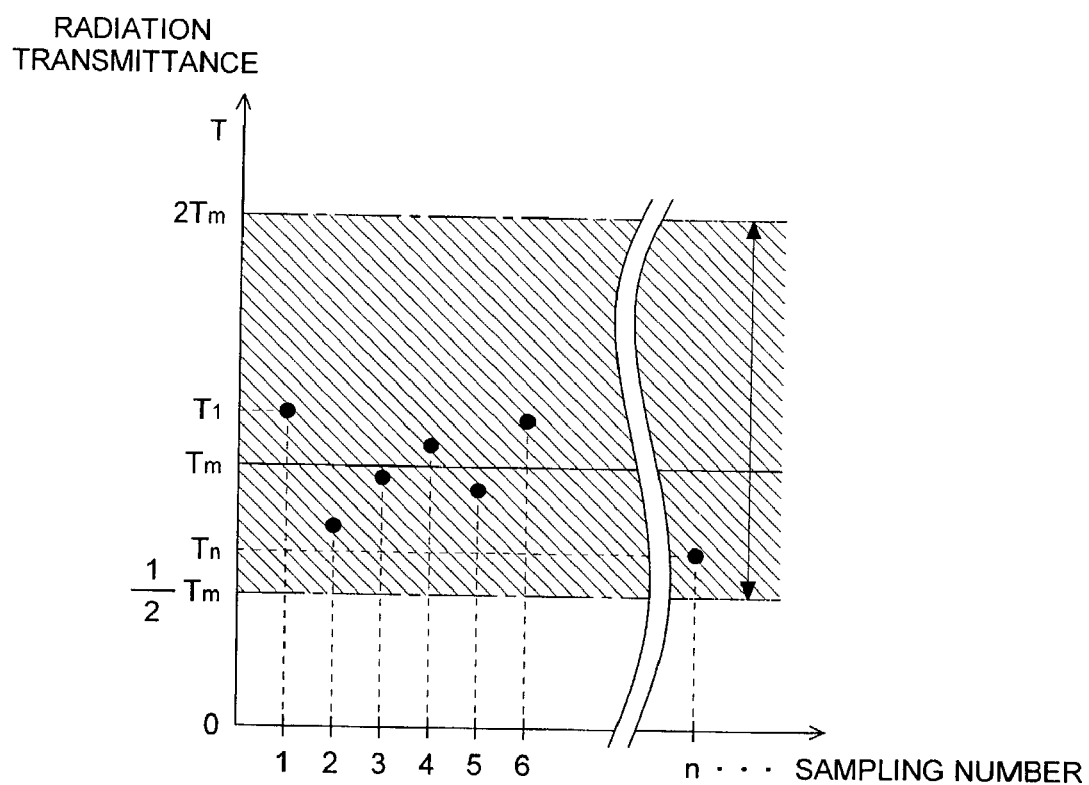

It is commonly said that the average radiation transmission factor of the local portion 21a of the area 1 mm$^2$ extracted from the surface of the metallic foil 21 (refer to FIG. 20(a)), is ½ times to 2 times of the average radiation transmission factor in the whole surface area. That is, when the average radiation transmission factor Tn for each of local portions (extraction number n) a plurality of which are arbitrarily extracted, is plotted in a graph of FIG. 20(b) in which the vertical axis expresses the radiation transmission factor and the horizontal axis expresses the extraction number n, each plotted point distributes in the area R (0.5 Tm≦T≦2 Tm, Tm: the average radiation transmission factor in the whole surface area of the metallic foil 21). This shows that the radiation transmission factor of the metallic foil 21 is comparatively uniform over the whole surface.

The thickness of the metallic foil 21 is defined that it is not lower than 5 $\mu$m and not larger than 200 $\mu$m. When the thickness is not larger than 5 $\mu$m, because the scattered ray removing function is not sufficiently performed, it is not preferable. Further, when the thickness is not lower than 200 $\mu$m, because the scattered ray by the metallic foil 21 affects the bad influence on the X-ray image, it is not preferable. In the present embodiment, the thickness of the metallic foil 21 is set to 12 $\mu$m.

Figure 21:
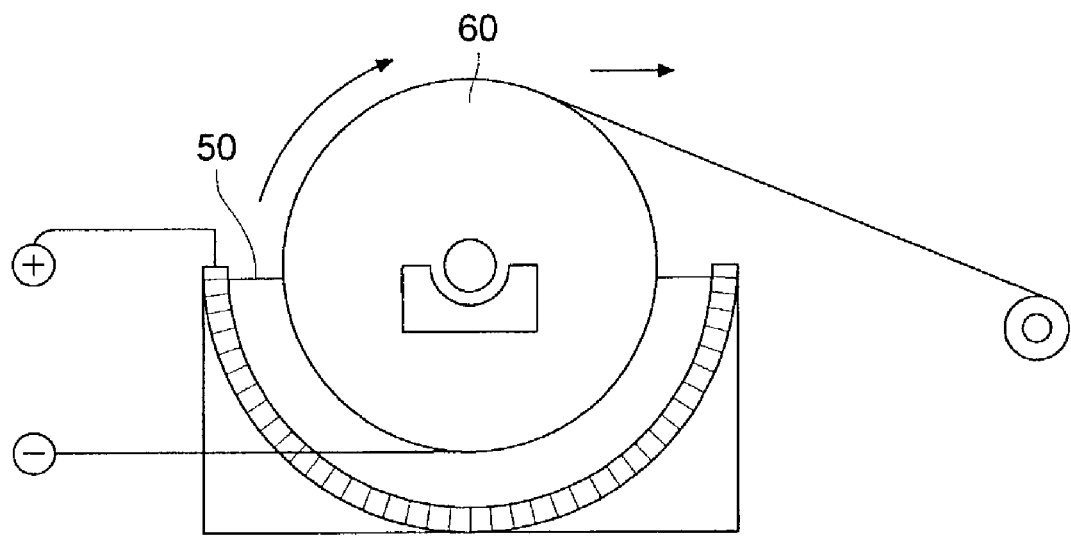
FIG. 21 is a conceptual drawing for illustrating a producing method (electrolytic solution method) of the metallic foil.
Figure 22:
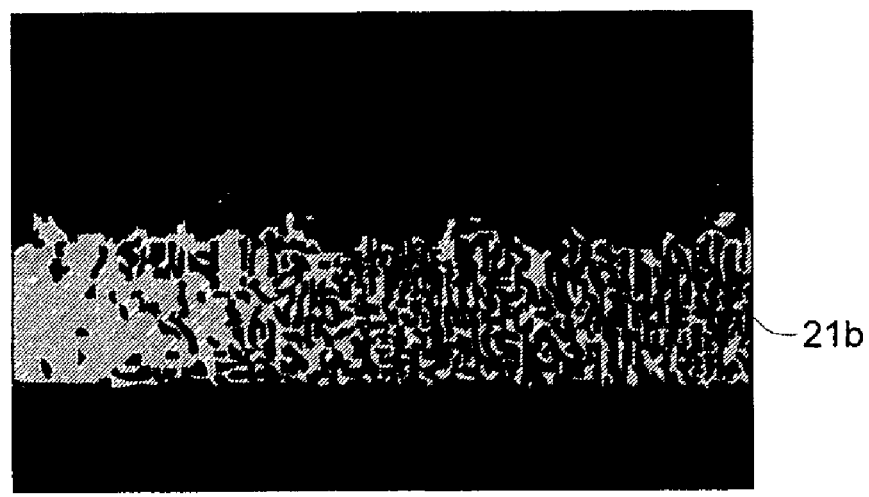
FIG. 22 is an enlarged section showing a columnar structure of the metallic foil.

The metallic foil 21 can be produced by an electrolyte method (refer to FIG. 21) by which the metal electrically adhered from the electrolyte 50 onto the rotation drum 60 is peeled and wound, or by rolling method by which the metallic line is rolled by a multistage mill. In the present embodiment, the electrolyte method is adopted, and the metallic foil 21 produced by the electrolyte method, as its cross section is shown in FIG. 22, has the pillar structure 21b. Accordingly, the X-ray parallel to the pillar direction (including the image information) can be effectively transmitted, and the scattered ray not parallel to the pillar direction (not including the image information) can be effectively cut off.

In the X-ray image reading apparatus according to the present embodiment, because, between the supporting plate 12 and the stimulable phosphor sheet 19, the metallic foil 21 structured by Cu is fixedly adhered, the X-ray of the low energy (scattering ray) scattered when it passes through the subject 40, can be effectively shielded. Further, because the thickness of this metallic foil 21 is set to 12 $\mu$m, the scattered ray due to this metallic foil 21 does not affect the bad influence on the X-ray image. Accordingly, the image quality of the X-ray image can be greatly increased.

Further, because the X-ray image reading apparatus according to the present embodiment adopts the metallic foil 21 having the pillar structure produced by the electrolyte method, the X-ray parallel to the pillar direction (including the image information) can be effectively transmitted, and the scattered ray not parallel to the pillar direction (not including the image information) can be effectively cut off.

Further, because the X-ray image reading apparatus according to the present embodiment adopts the carbon fiber reinforced resin as the material of the front plate 11a of the housing 11 and supporting plate 12, the transmission of the X-ray is not hindered, and the lowering of the image quality of the X-ray image can be prevented.

Figure 5:
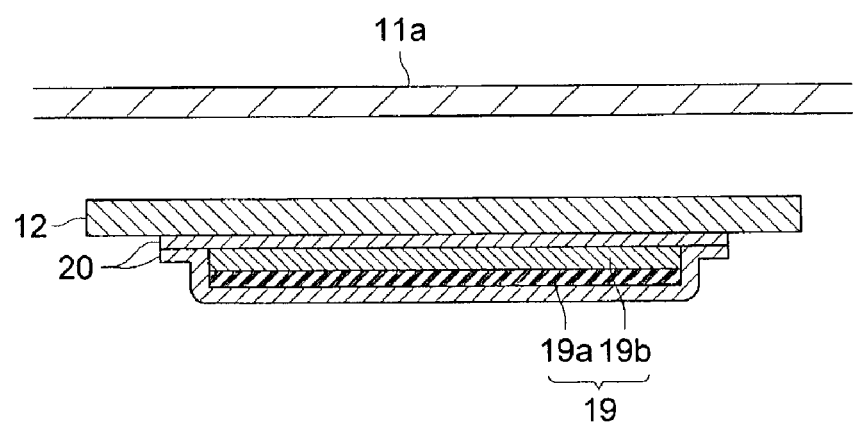
FIG. 5 is an enlarged section of part V of FIG. 4.
Figure 23:
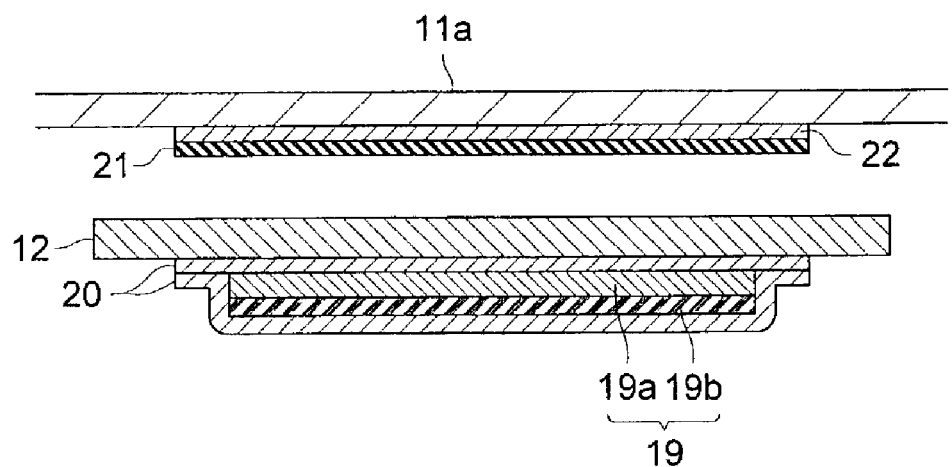
FIG. 23 is an example wherein the metallic foil is employed instead of the grid in FIG. 5

FIG. 23 shows an example in which the metallic foil is used instead of the grid in FIG. 5, and to the rear surface of the front plate 11a of the housing 11 (that is, the surface of the opposite side to the side onto which the X-ray is irradiated), the metallic foil 21 is adhered through the double-side adhesive tape 22. It is preferable that the double-side adhesive tape 22 is structured of polyester resin with the high X-ray transmission factor or polypropylene.

Figure 24:
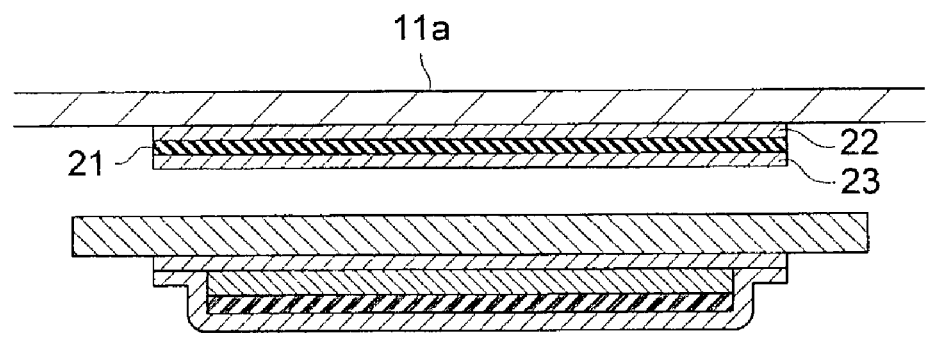
FIG. 24 is an enlarged section of the condition that a synthetic resin film is laminated on the metallic foil of the X-ray image reading apparatus shown in FIG. 23.

In this connection, in order to prevent the metallic foil 21 from being stained when the metallic foil 21 is exposed in the air for long period of time, as shown in FIG. 24, it is preferable that the synthetic resin film 23 is laminated on the other surface of the metallic foil 21 (the surface of the opposite side to the double-side adhesive tape 22). As the synthetic resin constituting this film 23, polyester resin such as polyethylene telephthalate, or polyethylene naphthalate which have the excellent moisture-proof property and high X-ray transmission factor, or polypropylene, can be listed.

The kind or thickness of the film 23 can be appropriately set by considering the kind or thickness of the metallic foil 21. For example, as described above, to the metallic foil 21 formed of Cu of 12 $\mu$m thickness, the polyethylene telephthalate film 23 of about 20 $\mu$m thickness can be adopted.

Figure 25:
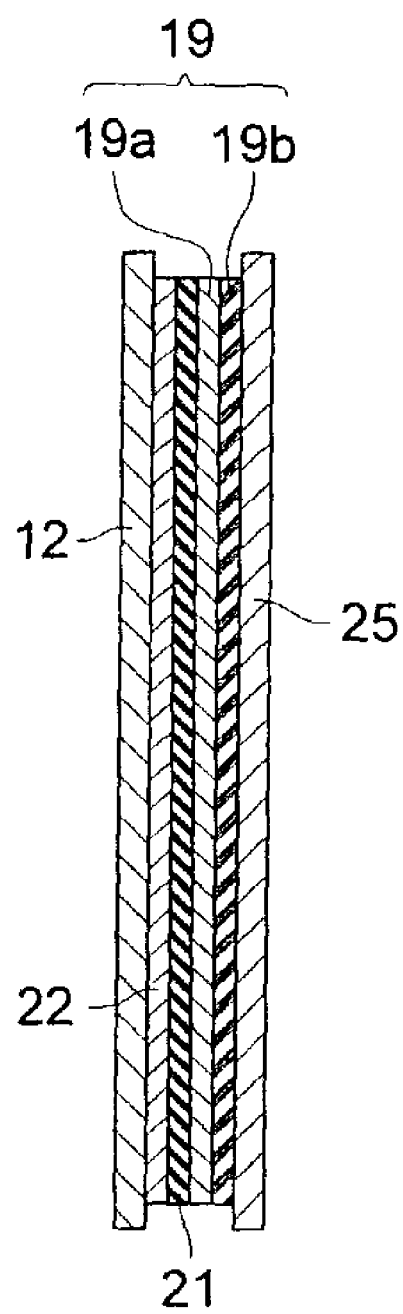
FIG. 25 is an example wherein the metallic foil is employed instead of the grid in FIG. 7.

FIG. 25 is a view showing an example using the metallic foil instead of the grid in FIG. 7, and to the rear surface of the supporting plate 12 (the surface of the opposite side to the side on which the X-ray is irradiated), the metallic foil 21 is adhered through the double-side adhesive tape 22, and at the time of the X-ray radiographing, the X-ray of the low energy scattered when the X-ray passes through the subject can be effectively removed. In this connection, in the same as the above-described embodiment, in order to prevent the metallic foil 21 from being stained when the metallic foil 21 is exposed in the air for long period of time, on the other surface of the metallic foil 21 (the surface opposite to the double-side adhesive tape), the synthetic resin film can also be laminated.

Figure 26:
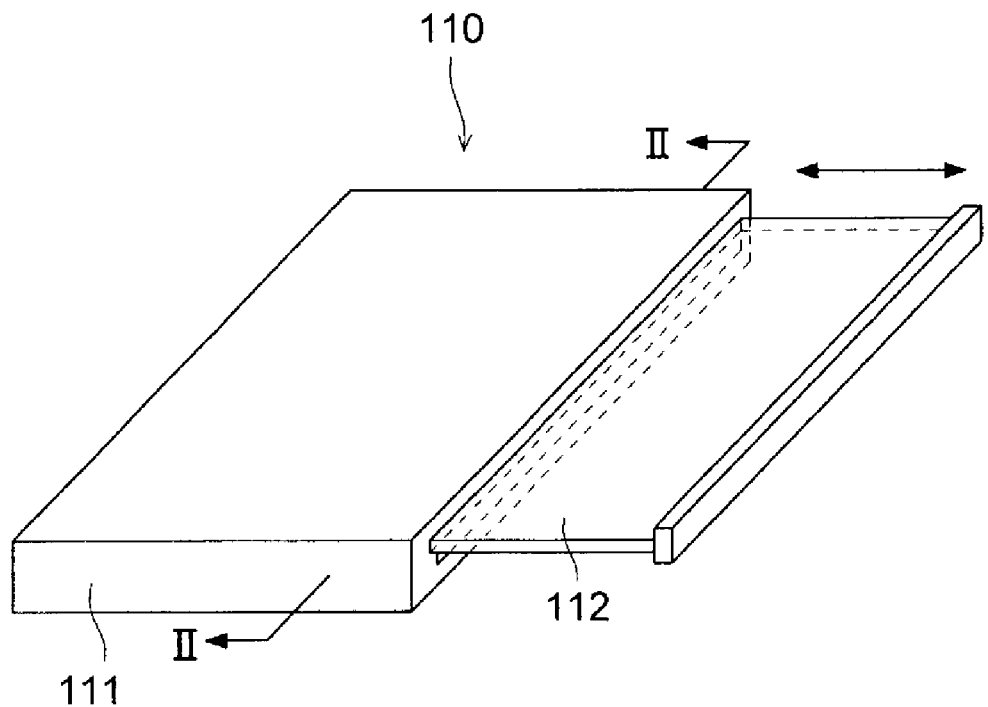
FIG. 26 is a schematic perspective view of a cassette related to the embodiment of the present invention.
Figure 27:
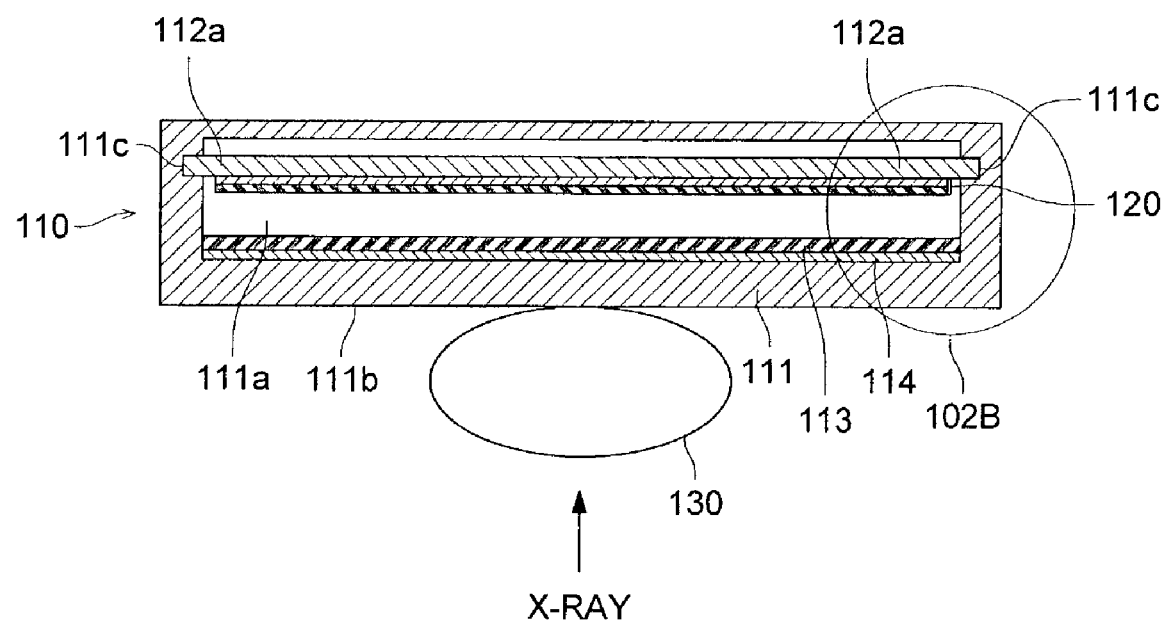
FIG. 27(a) is an enlarged section taken on line II—II section in FIG. 26.
FIG. 27(b) is an enlarged drawing of part 2B of FIG. 27(a).
Figure 27:
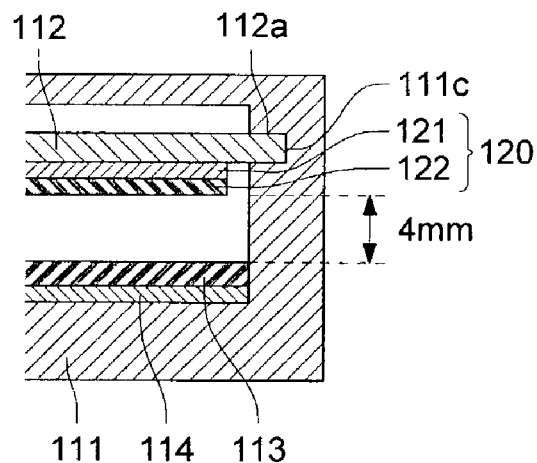

FIG. 26 shows an example in which the metallic foil is used instead of the grid in the cassette in FIG. 16. In FIG. 27(a), the metallic foil 113 is adhered to the rear surface of the front plate 111b of the housing 111 (that is, the surface of the opposite side to the side on which the X-ray is irradiated) through the double-side adhesive tape 114, and is a metallic layer which performs the function to remove the X-ray (scattering ray) of the low energy scattered when the X-ray passes through the subject 130 and the front plate 111b. It is preferable that the double-side adhesive tape 114 is structured of polyester resin with the high X-ray transmission factor, or polypropylene.

The stimulable phosphor sheet 120 in the present invention is temporarily fixed to the slide plate 112 by the fixing means, not shown, and following the slide operation of the slide plate 112, it is accommodated in the accommodation portion 111a of the housing 111 (refer to FIG. 27(a)). The thickness of the stimulable phosphor sheet 120 can be appropriately determined corresponding to the accumulated X-ray amount, the kind of the stimulable phosphor, and the height of the accommodation portion 111a of the housing 111. In this connection, in the present embodiment, as the fixing means, the double-side adhesive tape in which the lead foil to absorb the X-ray, exists, is adopted.

Further, in the present embodiment, the stimulable phosphor sheet 120 is arranged in the condition that it is separated by about 4 mm from the metallic foil 113 (refer to FIG. 27(b)). In this manner, by separating the stimulable phosphor sheet 120 from the metallic foil 113, when the stimulable phosphor sheet 120 is slid integrally with the slide plate 112, it can be prevented that the metallic foil 113 is brought into contact with the stimulable phosphor 122, and the physical damage and the optical deterioration of the stimulable phosphor 122 can be beforehand prevented.

In the cassette 110 according to the present embodiment, because, between the front plate 111b of the housing 111 and the stimulable phosphor sheet 120, because the metallic foil 113 structured by Cu is fixedly adhered, the X-ray of the low energy (scattering ray) scattered when it passes through the subject 130, can be effectively removed. Further, because the thickness of this metallic foil 113 is set to 12 μm, the scattering ray due to this metallic foil 113 does not affect the bad influence on the X-ray image. Accordingly, the image quality of the X-ray image can be greatly increased.

Further, because the cassette 110 according to the present embodiment adopts the metallic foil 113 having the pillar structure produced by the electrolyte method, the X-ray parallel to the pillar direction (including the image information) can be effectively transmitted, and the scattered ray not parallel to the pillar direction (not including the image information) can be effectively cut off.

Further, because the cassette 110 according to the present embodiment adopts the carbon fiber reinforced resin as the material of the housing 111, the transmission of the X-ray is not hindered, and by the excellent rigidity, the stimulable phosphor sheet 120 can be surely protected.

Figure 28:
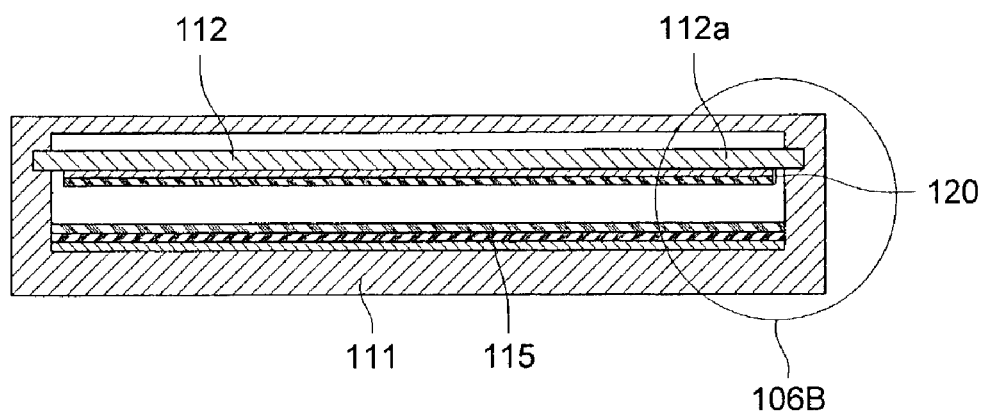
FIGS. 28(a) and 28(b) are for the purpose of explaining radiation transmittance for metallic foil of the cassette shown in FIG. 26.
Figure 28:
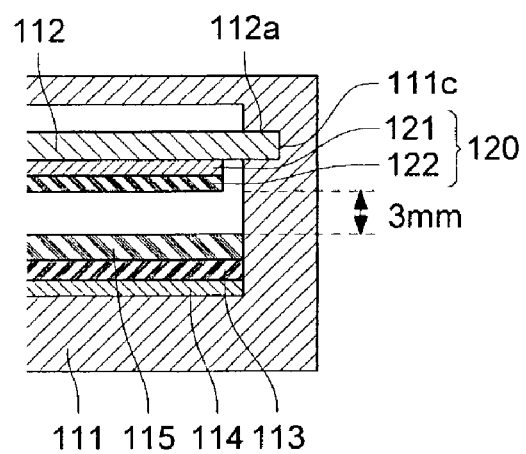

In this connection, in order to prevent the metallic foil 113 from being stained when the metallic foil 113 is exposed in the air for long period of time, as shown in FIG. 28, it is preferable that the synthetic resin film 115 is laminated on the other surface of the metallic foil 113 (the surface of the opposite side to the double-side adhesive tape 122). As the synthetic resin constituting this film 115, polyester resin such as polyethylene telephthalate, or polyethylene naphthalate which have the excellent moisture proof property and high X-ray transmission factor, or polypropylene, can be listed.

The kind or thickness of the film 115 can be appropriately set by considering the kind or thickness of the metallic foil 113. For example, as described above, to the metallic foil 113 formed of Cu of 12 μm thickness, the polyethylene telephthalate film 115 of about 20 μm thickness can be adopted. In this connection, as shown in FIG. 28(b), also in this case, the stimulable phosphor sheet 120 is arranged in the condition that it is about 3 mm separated from the metallic foil 113.

In this connection, in the embodiments described above, as the means by which the metallic foil 113 is fixedly adhered to the rear surface of the front plate 111b of the housing 111, the double-side adhesive tape 114 is adopted, however, the fixing means is not limited to this, for example, the metallic foil 113 may be adhered to the rear surface of the front plate 111b of the housing 111 through the adhesive agent. Also the adhesive agent in this case, it is preferable that it is structured of polyester resin with the high X-ray transmission factor.

(The Eighth Embodiment)

Next, an embodiment in which the present invention is applied to the X-ray detector having the semiconductor sensor, will be described.

Figure 29:
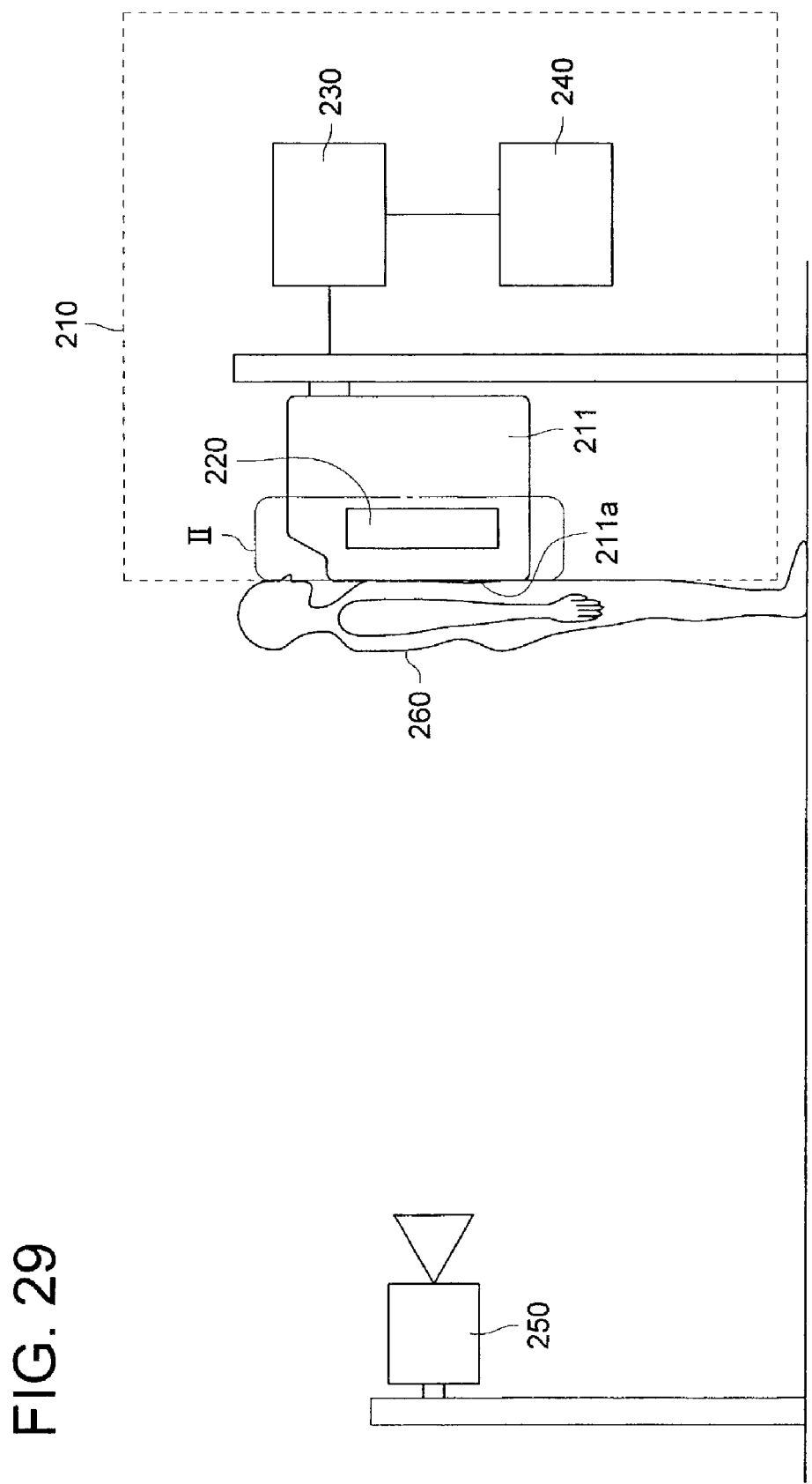
FIG. 29 is a schematic diagram of an X-ray image radiographing apparatus related to the eighth embodiment of the invention.

The X-ray image radiographing apparatus 210 according to the present embodiment, is provided, as shown in FIG. 29, with the housing 211, X-ray detector 220, image processing means 230, and image display means 240. The housing 211 mounts the X-ray detector 220 or each kind of the other devices in its inside, and is fixed at a predetermined position.

The X-ray radiographing is conducted by detecting the X-ray which is irradiated from the X-ray source 250 and which passes through the subject 260 and the front plate 211a of the housing 211, by the X-ray detector 220 (refer to FIG. 30), therefore, the front plate 211a of the housing 211 is produced by the material with the high X-ray transmission factor. In this connection, when the thickness of the front plate 211a is about 0.3–5 mm, because the penetrability of the X-ray is being secured and the maintaining of the strength can be intended, it is preferable. Further, it is preferable that the housing 211 is produced by the material with the comparatively high rigidity so that each kind of devices mounted in its inside can be surely protected.

Figure 30:
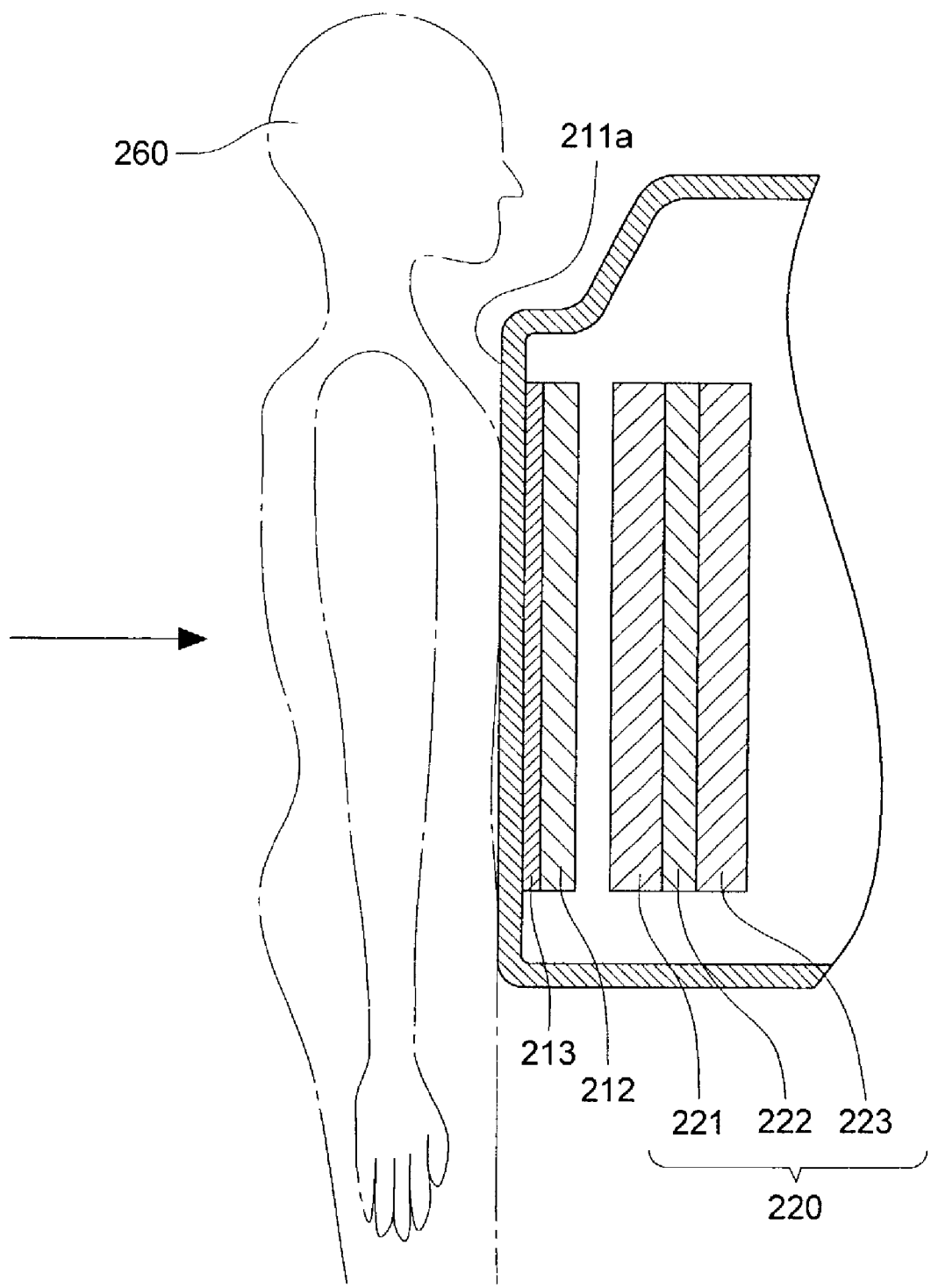
FIG. 30 is an enlarged section of part II in FIG. 29.

On the rear surface of the front plate 211a of the housing 211 (that is, the surface of the opposite side to the side on which the X-ray is irradiated), the metallic foil 212 is adhered through the double-side adhesive tape 213 (refer to FIG. 30). This metallic foil 212 is a metallic layer performing the function to remove the low energy X-ray (scattering ray) scattered when the X-ray passes through the subject 260 and the front plate 211a. It is preferable that the double-side adhesive tape 213 is structured of polyester resin which has the high X-ray transmission factor, or polypropylene.

In FIG. 30, the X-ray detector 220 is composed of the light emitting means 221, photoelectric conversion means 222, and supporting plate 223, and functions so that the irradiated X-ray is converted into the electric signal (image signal). The electric signal (image signal) converted by this X-ray detector 220 is sent to the image processing means 230, which will he described later, and displayed on the image display means 240. The X-ray detector 220 is fixed in the housing 211 by the fixing means, not shown.

The light emitting means 221 functions so that it emits the light corresponding to the intensity of the irradiated X-ray, and in the present embodiment, a scintillator is adopted. As the scintillator, the conventionally used one such as $Gd_2O_2$:Tb, fluorescent substance such as $CaWO_4$, scintillation fiber structured by doping the fluorescent substance in the fiber plate, CsI:Na, or CsI:Tl, can be used without limitation.

The light conversion means 222 generates the electric signal of the amount corresponding to the intensity of the light of the light emitting means 221, which is (light-emitted by the irradiation of the X-ray). The electric signal generated by the photoelectric conversion means 222 is sent to the image processing means 230 which will be described later, and displayed on the image display means 240. The supporting plate 223 is used for forming the photoelectric conversion means 222 on its upper surface, and in the present embodiment, the glass base plate is adopted.

As the photoelectric conversion means 222, the conventionally used one can be used without limitation. For example, a means or the like in which the thin film transistor (TFT) which is the switching element is formed on the supporting plate 223, and the PIN photodiode which is photoelectric conversion element is formed in the manner to connect to the TFT, (refer to Japanese Tokkai No. 2000-114530), can be listed.

The image processing means 230 is a means by which the electric signal transferred from the X-ray detector 220 is A/D converted and the digital signal is obtained. As the image output means 240, other than a device to display the X-ray image such as the CRT or liquid crystal display, a device to produce the hard-copy of the X-ray image such as the inkjet printer, can be listed.

In the X-ray image radiographing apparatus 210 according to the present embodiment, because, between the front plate 211a of the housing 211 and the X-ray detector 220, the metallic foil 212 structured by Cu is fixedly adhered, the X-ray of the low energy (scattering ray) scattered when it passes through the subject 260, can be effectively shielded in the condition that the uniformity is excellent. Further, because the thickness of this metallic foil 212 is set to 12 μm, the scattering ray due to this metallic foil 212 does not affect the bad influence on the X-ray image. Accordingly, the image quality of the X-ray image can be greatly increased.

Figure 31:
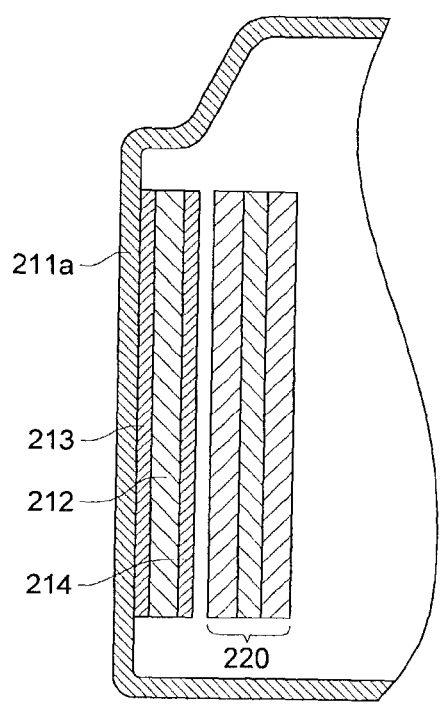
FIG. 31 is an enlarged section of the condition that a synthetic resin film is coated on the metallic foil of the X-ray image reading apparatus shown in FIG. 29.

In this connection, in order to prevent the metallic foil 212 from being stained when the metallic foil 212 is exposed in the air for long period of time, as shown in FIG. 31, it is preferable that the synthetic resin film 214 is laminated on the other surface of the metallic foil 212 (the surface of the opposite side to the double-side adhesive tape 213). As the synthetic resin constituting this film 214, polyester resin such as polyethylene telephthalate, or polyethylene naphthalate which have the excellent moisture proof property and high X-ray transmission factor, or polypropylene, can be listed.

In this connection, in the embodiments described above, as the means by which the metallic foil 212 is fixedly adhered to the rear surface of the front plate 211a of the housing 211, the double-side adhesive tape 213 is adopted, however, the fixing means is not limited to this, for example, the metallic foil 212 may be adhered to the rear surface of the front plate 211a of the housing 211 through the adhesive agent. Also the adhesive agent in this case, it is preferable that it is structured of polyester resin with the high X-ray transmission factor.

Figure 32:
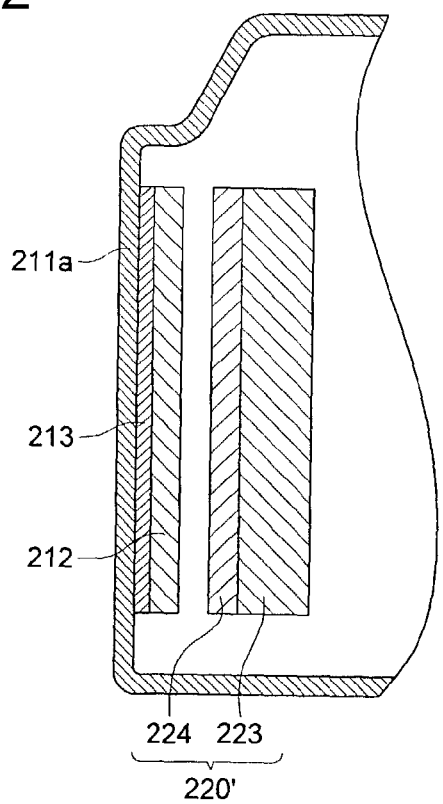
FIG. 32 is an enlarged section in the case of an occasion wherein the other X-ray detecting device is provided on the X-ray image padiographing apparatus, shown in FIG. 29.

Further, in the embodiment described above, the X-ray detector provided with the light emitting means is shown, however, as shown in FIG. 32, an X-ray detector 220' provided with the conversion means for directly converting the irradiated X-ray to the electric charge may also be adopted. This X-ray detector 220' is provided with a conversion means 224 by which the electric charge corresponding to the intensity of the irradiated X-ray is generated in the light conducting layer, and the generated electric charge is accumulated in a plurality of capacitors arranged plane-like, and the electric charge accumulated in the conversion means 224 is read out, and the radiation image can be obtained.

(The Ninth Embodiment)

Next, an example in which the present invention is applied to the X-ray image radiographing-use electronic cassette (electronic cassette) 310 housing the X-ray detector 320 for detecting the X-ray, will be described.

Figure 33:
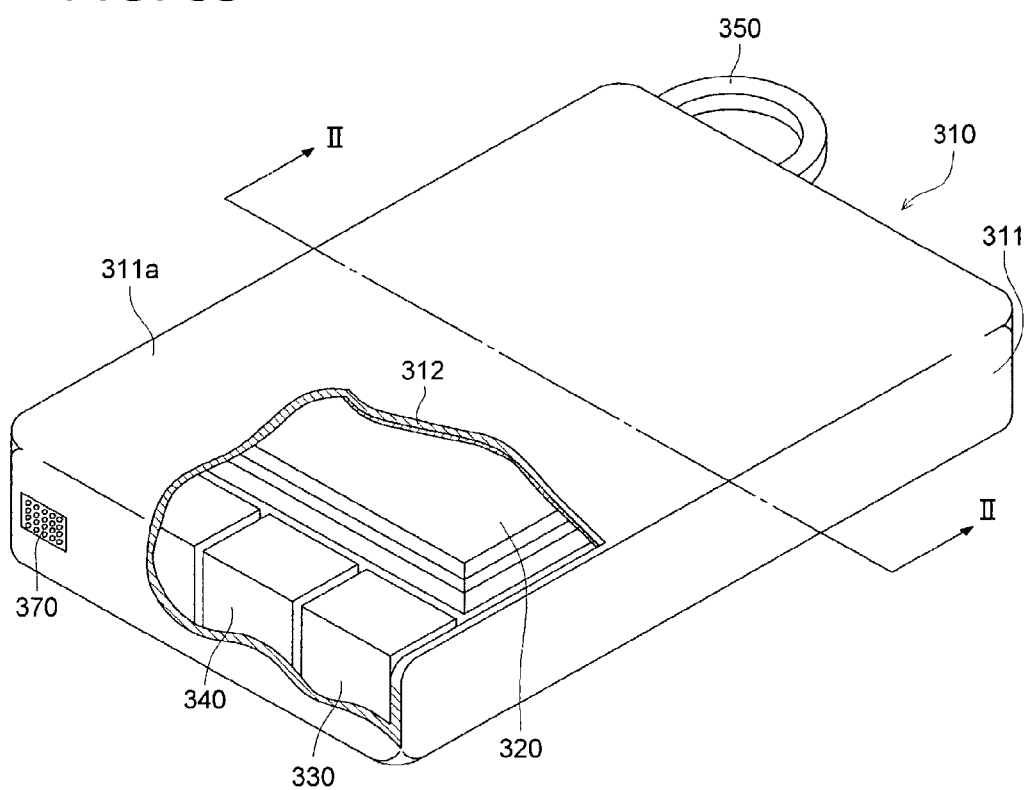
FIG. 33 is a schematic perspective view of an electronic cassette related to the ninth embodiment of the present invention.

The electronic cassette 310 according to the present embodiment shows the rectangular planar shape as shown in FIG. 33, and its handle 350 is held by the hand, and appropriately carried to a predetermined position in the hospital and can be used. This electronic cassette 310 is, as shown in FIG. 34, provided with a housing 311, metallic foil 312, x-ray detector 320, image information storing means 330 and battery 340.

The housing 311 is one to accommodate parts such as the x-ray detector 320, image information storing means 330 and battery 340, in its inside, and performs the function to prevent these accommodated parts from being damaged at the time of radiographing or conveying. The electronic cassette 310 according to the present embodiment is carried to the necessary position in the hospital, however, when assuming that a part of the body of the patient which is the subject 360 is placed on its upper portion, it is preferable that the housing 311 is produced by the material with the comparatively high rigidity.

Figure 34:
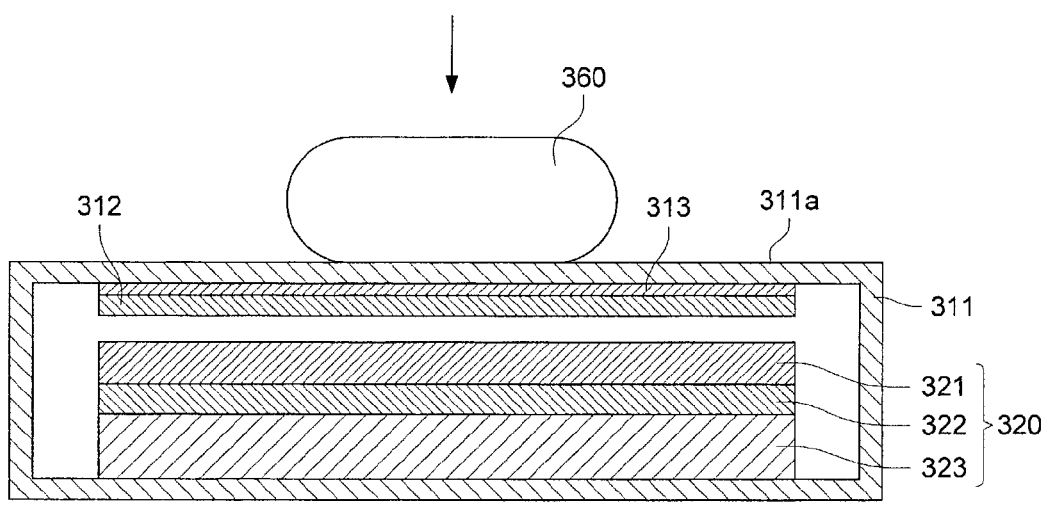
FIG. 34 is an enlarged section taken on line II—II in FIG. 33.

Further, the X-ray radiographing is conducted by detecting the X-ray which passes through the subject 360 and the front surface plate 311a of the housing 311, by the X-ray detector 320 (refer to FIG. 34). Therefore, the front plate 311a of the housing 311 is produced with the material having the high X-ray transmission factor. When the thickness of this front plate 311a is about 0.3–5 mm, because, while the penetrability of the X-ray is secured, the strength can be maintained, it is preferable.

The metallic foil 312 is adhered through the double-side adhesive tape 313 to the rear surface of the front plate 311a of the housing 311 (that is, the surface of the opposite side to the side on which the X-ray is irradiated), and is the metallic layer to perform the function to shield the low energy X-ray (scattering ray) scattered when the X-ray passes through the subject 360 and the front plate 311a. It is preferable that the double-side adhesive tape 313 is structured of polyester resin which has the high X-ray transmission factor, or polypropylene.

The X-ray detector 320 has the plane type structure structured by the light emitting means 321, photoelectric conversion means 322 and supporting plate 323, and functions so that the irradiated X-ray is converted into the electric signal (image signal). The converted electric signal (image signal) is sent to the outside image processing means connected to the electronic cassette 310, and displayed on the predetermined image display means.

The light emitting means 321 functions so that it emits the light corresponding to the intensity of the irradiated X-ray, and in the present embodiment, the scintillator is adopted. As the scintillator, the conventionally used one such as $Gd_2O_2$:Tb, fluorescent substance such as $CaWO_4$, scintillation fiber structured by doping the fluorescent substance in the fiber plate, CsI:Na, or CsI:Tl, can be used without limitation.

The light conversion means 322 generates the electric signal of the amount corresponding to the intensity of the light of the light emitting means 321, which is (light-emitted by the irradiation of the X-ray). The electric signal generated by the photoelectric conversion means 322 is sent to the outside image processing means connected to the electronic cassette 310, and displayed on a predetermined image display means. The supporting plate 323 is used for forming the photoelectric conversion means 322 on its upper surface, and in the present embodiment, the glass base plate is adopted.

As the photoelectric conversion means 322, the conventionally used one can be used without limitation. For example, a means or the like in which the thin film transistor (TFT) which is the switching element is formed on the supporting plate 323, and the PIN photodiode which is photoelectric conversion element is formed in the manner to connect to the TFT, (refer to Japanese Tokkai No. 2000-114530), can be listed.

The image information storing means 330 performs the function to temporarily store the electric signal (image signal) generated by the X-ray detector 320. When the image information storing means 330 is provided in the electronic cassette 310, a trouble in which the electric signal (image signal) obtained by the X-ray radiographing is outputted each time to the outside apparatus, can be omitted. Accordingly, while the arranged position of the electronic cassette 310 is changed, the X-ray radiographing can be continuously conducted in a plurality of times.

As the image information storing means 330, the conventionally used one such as RAM (Random Access Memory), magnetic recording medium, or optical recording medium, can be used without limitation. In this connection, in the electronic cassette 310, a CPU, not shown, is provided, and by the control of this CPU, the electric signal (image signal) stored in the image information storing means 330 is transferred to the outside image processing means through the connector 370.

The battery 340 is a unit for supplying the electricity to drive each kind of devices in the electric cassette 310. While this battery 340 is electrically charged, it is not necessary that the electricity is supplied from the outside to the electronic cassette 310, and the electronic cassette 310 can be used by properly being carried.

In the cassette 310 according to the present embodiment, because, between the front plate 311b of the housing 311 and the X-ray detector 320, because the metallic foil 312 structured by Cu is fixedly adhered, the X-ray of the low energy (scattered ray) scattered when it passes through the subject 360, can be effectively removed in the condition of the excellent uniformity. Further, because the thickness of this metallic foil 312 is set to 12 μm, the scattered ray due to this metallic foil 312 does not affect the bad influence on the X-ray image. Accordingly, the image quality of the X-ray image can be greatly increased.

Figure 35:
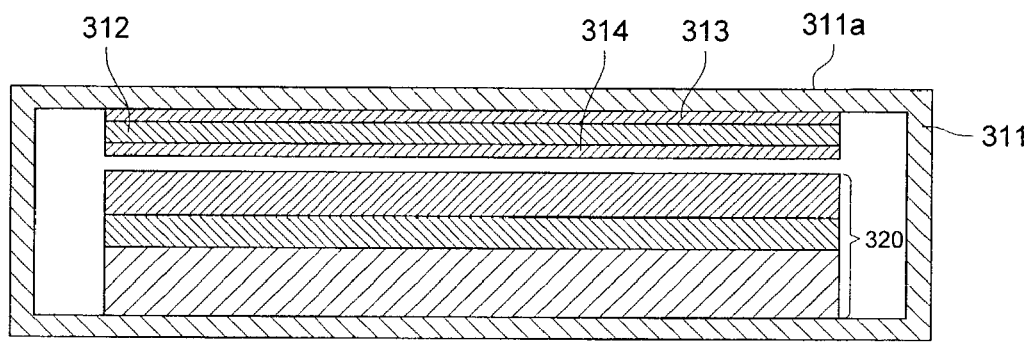
FIG. 35 is an enlarged section of the condition that a synthetic resin film is laminated on the metallic foil of the electronic cassette shown in FIG. 33.

In this connection, in order to prevent the metallic foil 312 from being stained when the metallic foil 312 is exposed in the air for long period of time, as shown in FIG. 35, it is preferable that the synthetic resin film 314 is laminated on the other surface of the metallic foil 312 (the surface of the opposite side to the double-side adhesive tape 313). As the synthetic resin constituting this film 314, polyester resin such as polyethylene telephthalate, or polyethylene naphthalate which have the excellent moisture proof property and high X-ray transmission factor, or polypropylene, can be listed.

Figure 36:
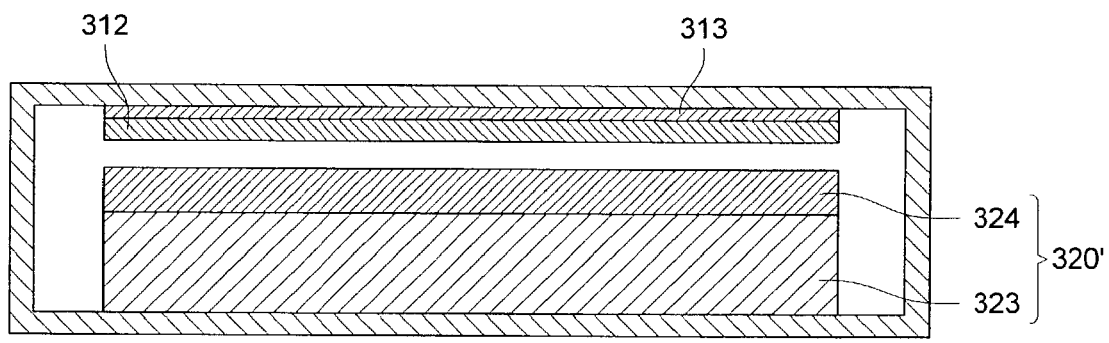
FIG. 36 is an enlarged section of the case wherein the other X-ray detecting device is provided on the electronic cassette shown in FIG. 33.
Figure 37:
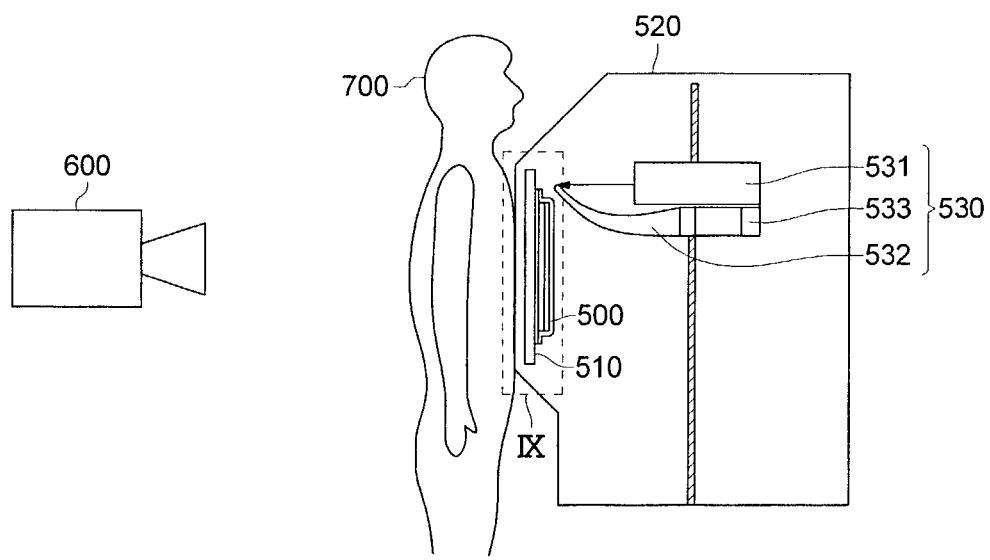
FIG. 37 is a schematic diagram of a conventional radiation image reading apparatus of a standing position type.
Figure 38:
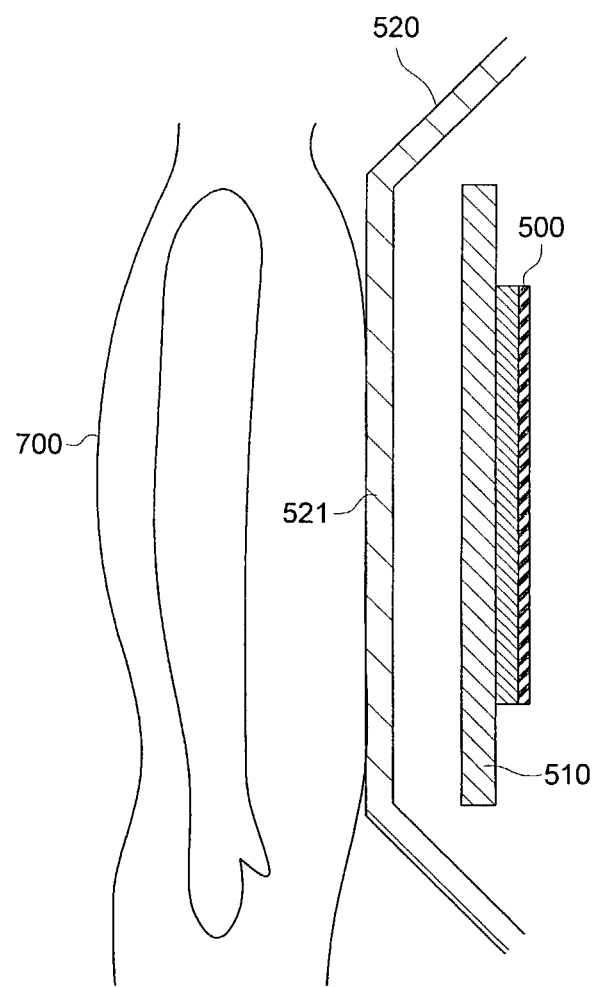
FIG. 38 is an enlarged section of part IX of FIG. 37.
Figure 39:
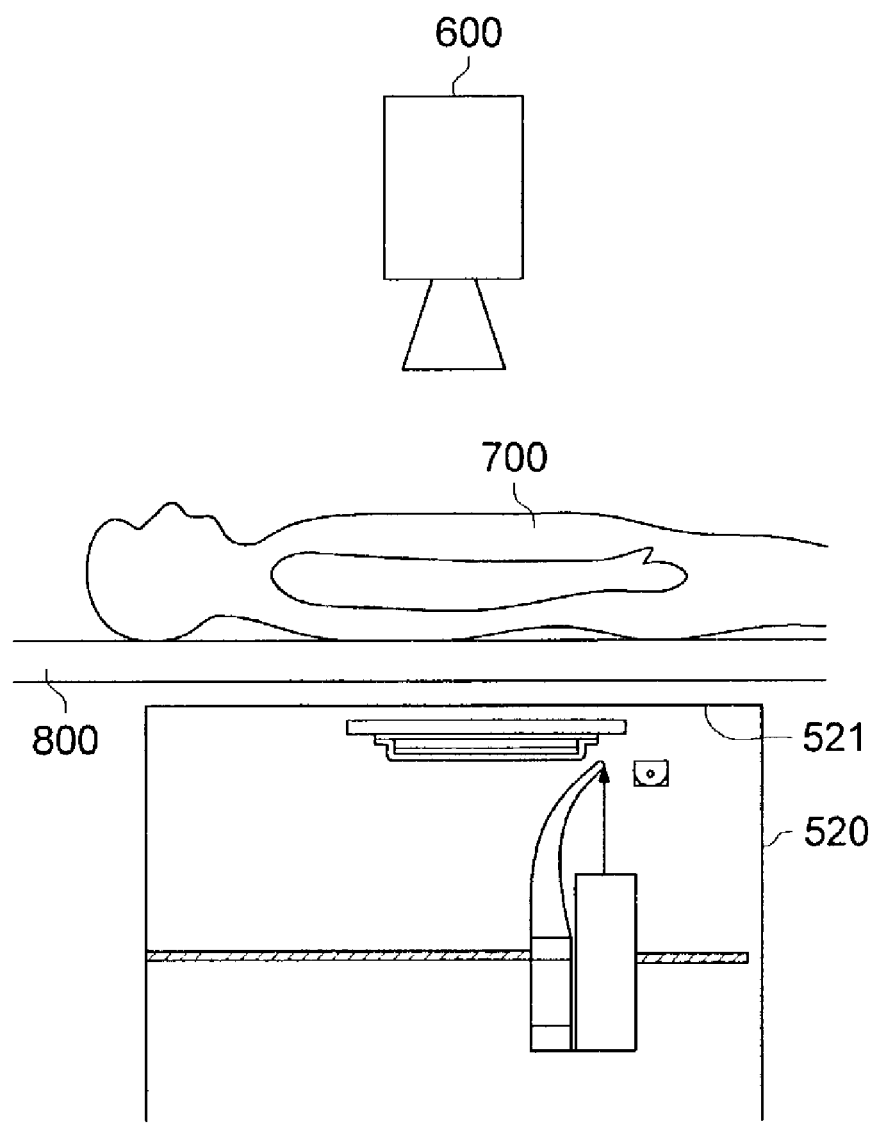
FIG. 39 is a schematic diagram of a conventional radiation image reading apparatus of a lying position type.

Further, in the embodiment described above, the X-ray detector provided with the light emission means is shown, however, as shown in FIG. 36, the X-ray detector 320' provided with the conversion means for converting the irradiated X-ray directly to the electric charge can be adopted. The X-ray detector 320' is provided with the conversion means 324 by which the electric charge corresponding to the intensity of the irradiated X-ray is generated in the light conducting layer, and the generated electric charge is accumulated in a plane-likely arranged plurality of capacitors, and the electric charge accumulated in the conversion means 324 is read out, and the radiation image can be obtained.

According to the present invention, by the grid to remove the scattered low energy radiation (scattered ray) generated at the time of the radiation radiographing, the image information according to the scattered ray can be prevented from being accumulated and recorded on the stimulable phosphor sheet. Particularly, when the grid is made as the supporting plate, because the supporting plate becomes unnecessary, and the scattered ray generated in the supporting plate is reduced, the influence of the scattered ray can be more reduced. Further, at the time of the radiation radiographing, because the grid is in contact with the stimulable phosphor sheet, in the stage in which the scattering of the scattered ray generated in the grid itself is smaller, the image information based on the radiation can be accumulated and recorded on the stimulable phosphor sheet, and by reading the accumulated and recorded image information, more accurate image information can be obtained.

According to the present invention, the low energy radiation (scattering ray) scattered when it passes through the subject, can be effectively shielded, and the image quality of the radiation image can be greatly increased.

What is claimed is:

1. A housing for accommodating a radiation detecting member, comprising:
    a radiation detecting member provided within the housing and having a radiation receiving surface to detect radiation incident from an outside of the housing; and
    a columnar-structured metallic member arranged at a radiation receiving surface side of the radiation detecting member to receive the radiation incident from the outside of the housing before the radiation detecting member receives the radiation and to reduce scattering radiation from the radiation before the radiation is detected by the radiation receiving surface.

2. The housing of claim 1, wherein the housing has a first plate member to which radiation is incident from the outside of the housing and which includes the columnar-structured metallic member.

3. The housing of claim 1, wherein the housing has a first plate member to which radiation is incident from the outside of the housing and which is formed by the columnar-structured metallic member.

4. The housing of claim 1, wherein the housing has a first plate member to which radiation is incident from the outside of the housing and wherein the columnar-structured metallic member is attached to an inner side of the first plate member.

5. The housing of claim 1, wherein the housing has a first plate member to which radiation is incident from the outside of the housing and wherein the columnar-structured metallic member is provided between the first plate member and the radiation detecting member.

6. The housing of claim 1, wherein the columnar-structured metallic member is attached to the radiation receiving surface of the radiation detecting member.

7. The housing of claim 1, wherein the housing is a casing of a radiation image reading apparatus in which a radiation image is read from the radiation detecting member.

8. The housing of claim 1, wherein the housing is shaped as a cassette adapted to be detachably installed in a radiation image reading apparatus.

9. The housing of claim 8, wherein the housing has a first plate member to which radiation is incident from the outside of the housing, the columnar-structured metallic member is attached to an inner surface of the first plate member, and the radiation detecting member is attached to the columnar-structured metallic member.

10. The housing of claim 8, wherein the housing has a first plate member to which radiation is incident from the outside of the housing, the first plate member is formed by the columnar-structured metallic member, and the radiation detecting member is attached to an inner surface of the columnar-structured metallic member.

11. The housing of claim 8, wherein the housing has a first plate member to which radiation is incident from the outside of the housing, the cassette has an opening section and the first plate member is detachably attached to the cassette so as to cover the opening section, and the columnar-structured metallic member and the radiation detecting member are mounted on the first plate member so that the columnar-structured metallic member and the radiation detecting member are separated from the cassette together with the first plate member.

12. The housing of claim 8, wherein the housing has a first plate member to which radiation is incident from the outside of the housing, the cassette comprises a slidable plate provided between the first plate member and the second plate member, and the radiation detecting member is mounted on the slidable plate so that the radiation detecting member is detached from the cassette together with the slidable plate.

13. The housing of claim 1, wherein an average radiation transmittance on a local part of 1 mm$^2$ sampled from the surface of the columnar-structured metallic member is from $1/10$ to 10 times that on a total area on the metallic surface, and further a thickness of the metallic member is in a range of 5 μm–200 μm.

14. The housing of claim 13, wherein the average radiation transmittance on a local part of 1 mm² sampled from the surface of the columnar-structured metallic member is from ½ to 2 times that on a total area on the metallic layer.

15. The housing of claim 13, wherein the columnar-structured metallic member is made of at least either one of Cu, Ni, Fe, Pb, Zn, W, Mo, Au, Ag, Ba, Ta, Cd, Ti, Zr, V, Nb, Cr, Co or Sn.

16. The housing of claim 13, wherein the columnar-structured metallic member is made of at least either one of Cu, Ni, Fe, Pb or Zn.

17. The housing of claim 13, wherein the columnar-structured metallic member comprises a metallic layer having an atomic number of not less than twenty, or an alloy having an effective atomic number of not less than twenty.

18. The housing of claim 13, wherein the columnar-structured metallic member is produced by an electrolyte solution method.

19. The housing of claim 13, wherein a synthetic resin thin film is coated on at least one of the surfaces of the metallic member.

20. The housing of claim 13, wherein the housing has a first plate member to which radiation is incident from the outside of the housing and the first plate member is made of at least either one material of carbon fiber reinforced resin, acrylic resin, phenol resin, polyimide resin or aluminum.

21. The housing of claim 1, wherein the radiation detecting member is a stimulable phosphor sheet.

22. The housing of claim 1, wherein the radiation detecting member is a photo-electrical converting member.

* * * * *